US008653064B2

(12) United States Patent
Armitage et al.

(10) Patent No.: US 8,653,064 B2
(45) Date of Patent: Feb. 18, 2014

(54) CRYSTALLINE FORMS OF SODIUM 4-{[9-CHLORO-7-(2-FLUORO-6-METHOXYPHENYL)-5H-PYRIMIDO[5,4-D][2]BENZAZEPIN-2-YL]AMINO}-2-METHOXYBENZOATE

(75) Inventors: Ian Armitage, Stoneham, MA (US);
Martin I. Cooper, Foxton (GB); Mark D. Eddleston, Nottingham (GB); Neil C. Faiber, Arlington, MA (US); Quentin J. McCubbin, Belmont, MA (US);
Stephen W. Watt, East Lothian (GB)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 211 days.

(21) Appl. No.: 13/027,523

(22) Filed: Feb. 15, 2011

(65) Prior Publication Data
US 2011/0245234 A1 Oct. 6, 2011

Related U.S. Application Data

(60) Provisional application No. 61/306,047, filed on Feb. 19, 2010.

(51) Int. Cl.
*A61P 35/00* (2006.01)
*A61K 31/55* (2006.01)
*C07D 487/02* (2006.01)

(52) U.S. Cl.
USPC .......................................... 514/215; 540/578

(58) Field of Classification Search
USPC .......................................... 514/215; 540/578
See application file for complete search history.

(56) References Cited

U.S. PATENT DOCUMENTS

| 5,747,487 | A | 5/1998 | Albright et al. |
| 7,572,784 | B2 | 8/2009 | Claiborne et al. |
| 7,718,648 | B2 | 5/2010 | Claiborne et al. |
| 8,026,246 | B2 | 9/2011 | Claiborne et al. |
| 2007/0104785 | A1 | 5/2007 | Navale et al. |
| 2007/0149561 | A1 | 6/2007 | Dhanak et al. |
| 2007/0185087 | A1 | 8/2007 | Claiborne et al. |
| 2009/0299060 | A1 | 12/2009 | Claiborne et al. |
| 2010/0183601 | A1 | 7/2010 | Manfredi |
| 2010/0310651 | A1 | 12/2010 | Mittal |
| 2011/0039826 | A1 | 2/2011 | Ramanan et al. |
| 2011/0312942 | A1 | 12/2011 | Claiborne et al. |
| 2011/0312943 | A1 | 12/2011 | Claiborne et al. |

FOREIGN PATENT DOCUMENTS

| WO | WO 01/10462 A1 | 2/2001 |
| WO | WO 2008/005266 A2 | 1/2008 |
| WO | WO 2009/070652 A1 | 6/2009 |

OTHER PUBLICATIONS

International Search Report dated Apr. 11, 2011 from International Application No. PCT/US2011/24883, which relates to U.S. Appl. No. 13/027,523.
International Search Report and Written Opinion dated Jul. 30, 2010 from International Application No. PCT/US2010/001434, which relates to U.S. Appl. No. 12/780,015, filed May 14, 2010.
International Search Report dated Jul. 10, 2010 from International Application No. PCT/US2010/002109, which relates to U.S. Appl. No. 12/844,920.
International Search Report dated Jan. 3, 2010 from International Application No. PCT/US2009/006560, which relates to U.S. Appl. No. 12/638,018.
Faure, A. et al., "Process Control and Scale-up of Pharmaceutical Wet Granulation Processes: A Review", *European Journal of Pharmaceutics and Biopharmaceutics*, vol. 52, No. 3, (Nov. 1, 2001), pp. 269-277.
Trybulski, E. et al., "2-Benzazepines. 5.[1,2] Synthesis of Pyrimido[5,4-*d*][2]benzazepines and Their Evaluation as Anxiolytic Agents", *Journal of Medicinal Chemistry*, vol. 26, No. 11, (1983), pp. 1596-1601.
Yakushijin, Yoshihro et al., "The Expression of the Aurora-A Gene and Its Significance with Tumorgenesis in Non-Hodgkin's Lymphoma", *Leukemia and Lymphoma*, vol. 45, No. 9, (Sep. 2004), pp. 1741-1746.
Caira, M.R., Crystalline Polymorphism of Organic Compounds, Topics in Current Chemistry, 198:163-208 (1998).

*Primary Examiner* — Brenda Coleman
(74) *Attorney, Agent, or Firm* — Choate Hall & Stewart LLP; Andrea L. C. Robidoux

(57) ABSTRACT

The present invention is directed to a compound of formula (I):

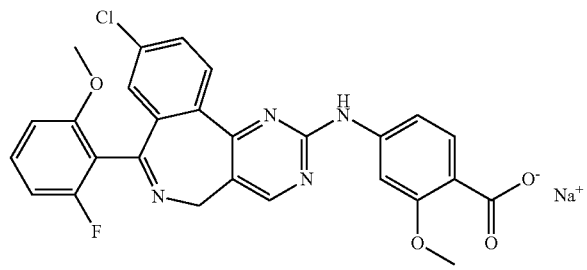

or a crystalline form thereof, or a solvate thereof; to a solid pharmaceutical composition comprising a pharmaceutically effective amount of the compound of formula (I), or a crystalline form thereof, or a solvate thereof, and at least one pharmaceutically acceptable carrier or diluent, and to the use of a compound of formula (I), or a crystalline form thereof, or a solvate thereof, for treating a patient suffering from, or subject to, a disease, disorder, or condition mediated by Aurora kinase, and methods related thereto.

20 Claims, 19 Drawing Sheets

CRYSTALLINE FORMS OF SODIUM 4-{[9-CHLORO-7-(2-FLUORO-6-METHOXYPHENYL)-5H-PYRIMIDO[5,4-D][2]BENZAZEPIN-2-YL]AMINO}-2-METHOXYBENZOATE

PRIORITY CLAIM

The present application claims the benefit of U.S. Provisional Application Ser. No. 61/306,047, filed Feb. 19, 2010 (pending), which is hereby incorporated by reference in its entirety.

FIELD OF THE INVENTION

The present invention relates to sodium 4-{[9-chloro-7-(2-fluoro-6-methoxyphenyl)-5H-pyrimido[5,4-d][2]benzazepin-2-yl]amino}-2-methoxybenzoate of formula (I):

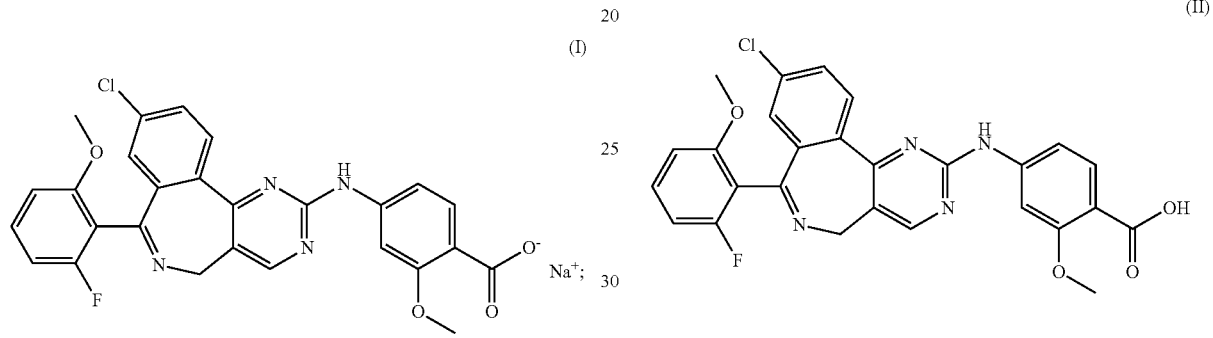

(I)

or a crystalline form thereof, or a solvate thereof.

The invention is also directed to a process for the synthesis of crystalline forms of formula (I). The invention is also directed to the pharmaceutical use of crystalline forms of formula (I) as an Aurora kinase inhibitor, solid pharmaceutical compositions comprising the crystalline forms of the invention, and methods of making such pharmaceutical compositions.

BACKGROUND OF THE INVENTION

According to the American Cancer Society, approximately 560,000 Americans died from cancer during 2006, while 2007 brought an estimated 12 million new cancer cases worldwide. Although medical advances have improved cancer survival rates, there is a continuing need for new and more effective treatment.

Cancer is characterized by uncontrolled cell reproduction. Mitosis is a stage in the cell cycle during which a series of complex events ensure the fidelity of chromosome separation into two daughter cells. Several current cancer therapies, including the taxanes and vinca alkaloids, act to inhibit the mitotic machinery. Mitotic progression is largely regulated by proteolysis and by phosphorylation events that are mediated by mitotic kinases. Aurora kinase family members (e.g., Aurora A, Aurora B, Aurora C) regulate mitotic progression through modulation of centrosome separation, spindle dynamics, spindle assembly checkpoint, chromosome alignment, and cytokinesis (Dutertre et al., *Oncogene,* 21: 6175 (2002)); Berdnik et al., *Curr. Biol.,* 12: 640 (2002)). Overexpression and/or amplification of Aurora kinases have been linked to oncogenesis in several tumor types including those of colon and breast (Warner et al., *Mol. Cancer Ther.,* 2: 589 (2003); Bischoff et al., *EMBO,* 17: 3062 (1998); Sen et al., *Cancer Res.,* 94: 1320 (2002)). Moreover, Aurora kinase inhibition in tumor cells results in mitotic arrest and apoptosis, suggesting that these kinases are important targets for cancer therapy (Ditchfield, J. *Cell Biol.,* 161: 267 (2003); Harrington et al., *Nature Med.,* 1 (2004)). Given the central role of mitosis in the progression of virtually all malignancies, inhibitors of the Aurora kinases are expected to have application across a broad range of human tumors.

WO 05/111039, U.S. Pat. No. 7,572,784, US Publication No. 2007/0185087, US Publication No. 2008/0045501, WO 08/063525, US Publication No. 2008/0167292, and US Publication No. 2010/0310651 hereby incorporated by reference in their entirety, disclose compounds that inhibit Aurora kinase enzymes. For example, the compound 4-{[9-chloro-7-(2-fluoro-6-methoxyphenyl)-5H-pyrimido[5,4-d][2]benzazepin-2-yl]amino}-2-methoxybenzoic acid of formula (II):

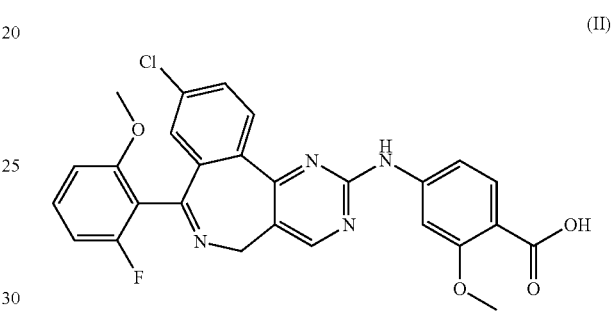

(II)

is a small molecule inhibitor of Aurora kinase.

These applications additionally disclose methods for the preparation of these compounds, pharmaceutical compositions containing these compounds, and methods for the prophylaxis and therapy of diseases, disorders, or conditions associated with overexpression and/or amplification of Aurora kinases, including, but not limited to, cell proliferative disorders such as cancer.

Sodium 4-{[9-chloro-7-(2-fluoro-6-methoxyphenyl)-5H-pyrimido[5,4-d][2]benzazepin-2-yl]amino}-2-methoxybenzoate (I) is described in WO 08/063525 and U.S. Ser. No. 08/0167292, herein incorporated by reference in their entirety. These references describe the synthesis of the compound of formula (I), which results in a mixture of crystalline forms, Form 1 and Form 2, of sodium 4-{[9-chloro-7-(2-fluoro-6-methoxyphenyl)-5H-pyrimido[5,4-d][2]benzazepin-2-yl]amino}-2-methoxybenzoate. These applications do not disclose other specific salts or crystalline forms of 4-{[9-chloro-7-(2-fluoro-6-methoxyphenyl)-5H-pyrimido[5,4-d][2]benzazepin-2-yl]amino}-2-methoxybenzoic acid (II).

The large-scale manufacturing of a pharmaceutical composition poses many challenges to the chemist and chemical engineer. While many of these challenges relate to the handling of large quantities of reagents and control of large-scale reactions, the handling of the final product poses special challenges linked to the nature of the final active product itself. Not only must the product be prepared in high yield, be stable, and capable of ready isolation, the product must possess properties that are suitable for the types of pharmaceutical preparations in which they are likely to be ultimately used. The stability of the active ingredient of the pharmaceutical preparation must be considered during each step of the manufacturing process, including the synthesis, isolation, bulk storage, pharmaceutical formulation and long-term formulation. Each of these steps may be impacted by various environmental conditions of temperature and humidity.

The pharmaceutically active substance used to prepare the pharmaceutical compositions should be as pure as possible, and its stability on long-term storage must be guaranteed under various environmental conditions. These properties are absolutely essential to prevent the appearance of unintended degradation products in pharmaceutical compositions, which degradation products may be potentially toxic or result simply in reducing the potency of the composition.

A primary concern for the manufacture of large-scale pharmaceutical compounds is that the active substance should have a stable crystalline morphology to ensure consistent processing parameters and pharmaceutical quality. If an unstable crystalline form is used, crystal morphology may change during manufacture and/or storage resulting in quality control problems, and formulation irregularities. Such a change may affect the reproducibility of the manufacturing process and thus lead to final formulations which do not meet the high quality and stringent requirements imposed on formulations of pharmaceutical compositions. In this regard, it should be generally borne in mind that any change to the solid state of a pharmaceutical composition which can improve its physical and chemical stability gives a significant advantage over less stable forms of the same drug.

When a compound crystallizes from a solution or slurry, it may crystallize with different spatial lattice arrangements, a property referred to as "polymorphism." Each of the crystal forms is a "polymorph." While polymorphs of a given substance have the same chemical composition, they may differ from each other with respect to one or more physical properties, such as solubility and dissociation, true density, melting point, crystal shape, compaction behavior, flow properties, and/or solid state stability.

As described generally above, the polymorphic behavior of drugs can be of great importance in pharmacy and pharmacology. The differences in physical properties exhibited by polymorphs affect practical parameters such as storage stability, compressibility and density (important in formulation and product manufacturing), and dissolution rates (an important factor in determining bio-availability). Differences in stability can result from changes in chemical reactivity (e.g., differential oxidation, such that a dosage form discolors more rapidly when it is one polymorph than when it is another polymorph) or mechanical changes (e.g., tablets crumble on storage as a kinetically favored polymorph converts to thermodynamically more stable polymorph) or both (e.g., tablets of one polymorph are more susceptible to breakdown at high humidity). In addition, the physical properties of the crystal may be important in processing: for example, one polymorph might be more likely to form solvates that cause the solid form to aggregate and increase the difficulty of solid handling, or might be difficult to filter and wash free of impurities (i.e., particle shape and size distribution might be different between one polymorph relative to other).

While drug formulations having improved chemical and physical properties are desired, there is no predictable means for preparing new drug forms (e.g., polymorphs) of existing molecules for such formulations. These new forms would provide consistency in physical properties over a range of environments common to manufacturing and composition usage. More particularly, there is a need for an inhibitor of Aurora kinase, including in particular Aurora A or B. Such an inhibitor should have utility in treating a patient suffering from or subject to Aurora kinase mediated pathological (diseases) conditions involving cell survival, proliferation and migration, including chronic inflammatory proliferative disorders, e.g., psoriasis and rheumatoid arthritis; proliferative ocular disorders, e.g., diabetic retinopathy; benign proliferative disorders, e.g., hemangiomas; and cancer, as well as having properties suitable for large-scale manufacturing and formulation.

SUMMARY OF THE INVENTION

The present invention is directed to sodium 4-{[9-chloro-7-(2-fluoro-6-methoxyphenyl)-5H-pyrimido[5,4-d][2]benzazepin-2-yl]amino}-2-methoxybenzoate of formula (I), or a crystalline form thereof, or a solvate thereof. These forms have properties that are useful for large-scale manufacturing, pharmaceutical formulation, and storage. The present invention also provides solid pharmaceutical compositions comprising said crystalline forms, and methods for uses of said crystalline forms, for the treatment of a variety of diseases, disorders or conditions as described herein.

One embodiment of the invention is directed toward sodium 4-{[9-chloro-7-(2-fluoro-6-methoxyphenyl)-5H-pyrimido[5,4-d][2]benzazepin-2-yl]amino}-2-methoxybenzoate (I), wherein the Sodium Salt is a single crystalline form; the possible single crystalline forms being described herein.

Another embodiment of the invention is directed to a solid pharmaceutical composition comprising at least one pharmaceutically acceptable carrier or diluent; and sodium 4-{[9-chloro-7-(2-fluoro-6-methoxyphenyl)-5H-pyrimido[5,4-d][2]benzazepin-2-yl]amino}-2-methoxybenzoate (I), wherein the Sodium Salt is a single crystalline form; the possible single crystalline forms being described herein.

Another embodiment of the invention is directed to the use of sodium 4-{[9-chloro-7-(2-fluoro-6-methoxyphenyl)-5H-pyrimido[5,4-d][2]benzazepin-2-yl]amino}-2-methoxybenzoate (I), wherein the Sodium Salt is a single crystalline form; to prepare a pharmaceutical composition, the possible single crystalline forms being described herein.

Other embodiments of the invention are directed toward methods of treating a subject in need of an Aurora kinase inhibitor or a subject with cancer by administering an effective amount of a crystalline form of sodium 4-{[9-chloro-7-(2-fluoro-6-methoxyphenyl)-5H-pyrimido[5,4-d][2]benzazepin-2-yl]amino}-2-methoxybenzoate (I), wherein the Sodium Salt is a single crystalline form; the possible single crystalline forms being described herein.

Other embodiments of the invention are also directed to methods of preparing crystalline forms of sodium 4-{[9-chloro-7-(2-fluoro-6-methoxyphenyl)-5H-pyrimido[5,4-d][2]benzazepin-2-yl]amino}-2-methoxybenzoate (I), wherein the Sodium Salt is a single crystalline form, the possible single crystalline forms being described herein.

The present invention shall be more fully discussed with the aid of the following figures and detailed description below.

DETAILED DESCRIPTION OF THE INVENTION

Definitions and Abbreviations

Figure 1:
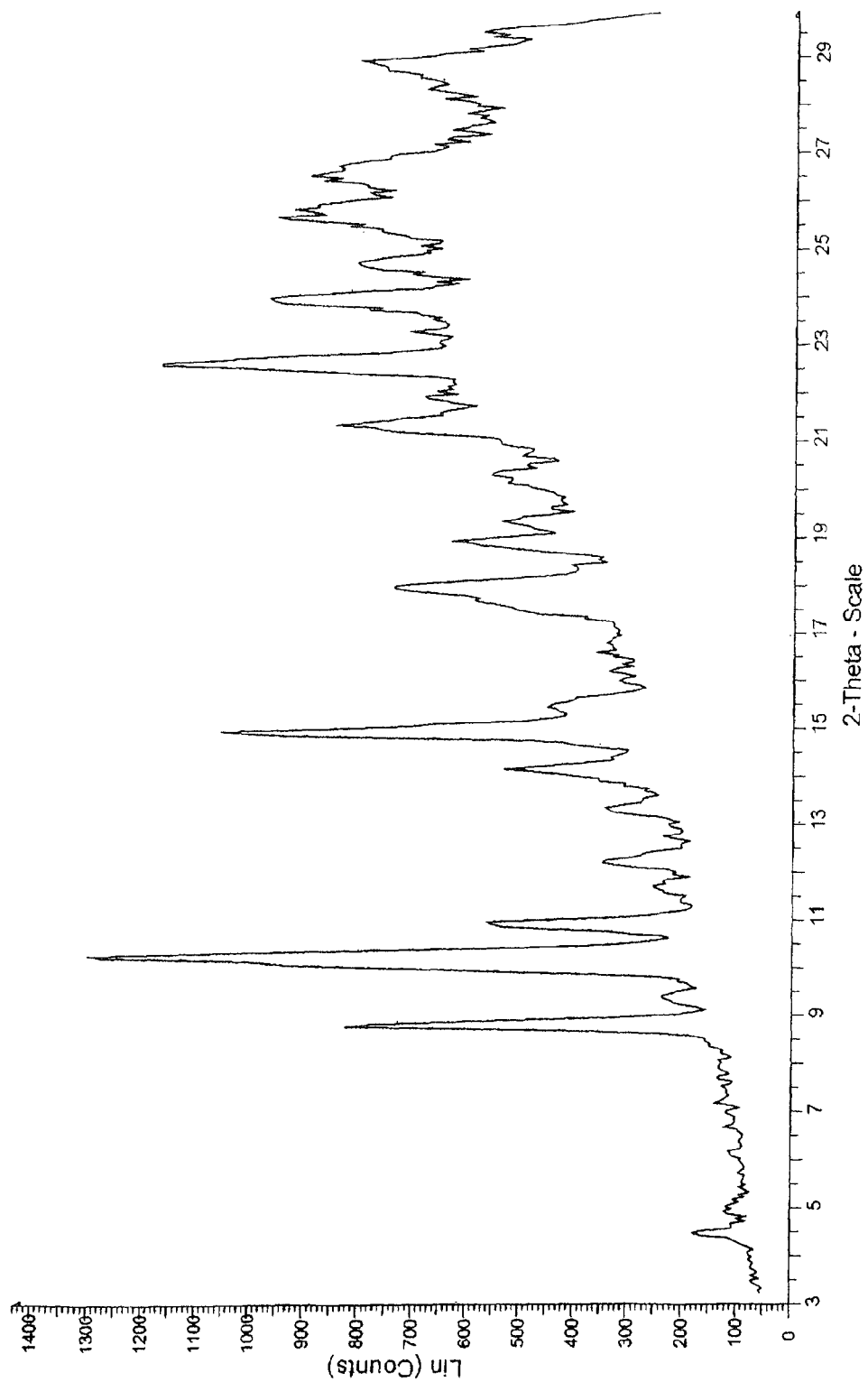
FIG. 1 is a powder X-ray diffractogram (XRPD) of sodium 4-{[9-chloro-7-(2-fluoro-6-methoxyphenyl)-5H-pyrimido [5,4-d][2]benzazepin-2-yl]amino}-2-methoxybenzoate Form 1.

As used above, and throughout the description of the invention, the following terms, unless otherwise indicated, shall be understood to have the following meanings.

"Sodium Salt" is meant to describe the sodium salt of 4-{[9-chloro-7-(2-fluoro-6-methoxyphenyl)-5H-pyrimido [5,4-d][2]benzazepin-2-yl]amino}-2-methoxybenzoic acid, and has the structure of formula (I).

"Form 1" or "sodium 4-{[9-chloro-7-(2-fluoro-6-methoxyphenyl)-5H-pyrimido[5,4-d][2]benzazepin-2-yl]amino}-2-methoxybenzoate Form 1" are used interchangeably, and describe Form 1 of sodium 4-{[9-chloro-7-(2-fluoro-6-methoxyphenyl)-5H-pyrimido[5,4-d][2]benzazepin-2-yl] amino}-2-methoxybenzoate, as synthesized in Example 3, Method B, in the Examples section below, and as described below, and represented by data shown in FIGS. 1, 2, and 3.

"Form 2" or "sodium 4-{[9-chloro-7-(2-fluoro-6-methoxyphenyl)-5H-pyrimido[5,4-d][2]benzazepin-2-yl]amino}-2-methoxybenzoate Form 2" are used interchangeably, and describe Form 2 of sodium 4-{[9-chloro-7-(2-fluoro-6-methoxyphenyl)-5H-pyrimido[5,4-d][2]benzazepin-2-yl] amino}-2-methoxybenzoate, as synthesized in Example 3, Method A, in the Examples section below, and as described below, and represented by data shown in FIGS. 4, 5, and 6.

"Form 4" or "sodium 4-{[9-chloro-7-(2-fluoro-6-methoxyphenyl)-5H-pyrimido[5,4-d][2]benzazepin-2-yl]amino}-2-methoxybenzoate Form 4" are used interchangeably, and describe Form 4 of sodium 4-{[9-chloro-7-(2-fluoro-6-methoxyphenyl)-5H-pyrimido[5,4-d][2]benzazepin-2-yl] amino}-2-methoxybenzoate, as synthesized in Example 4, in the Examples section below, and as described below, and represented by data shown in FIG. 7.

"Form 6" or "sodium 4-{[9-chloro-7-(2-fluoro-6-methoxyphenyl)-5H-pyrimido[5,4-d][2]benzazepin-2-yl]amino}-2-methoxybenzoate Form 6" are used interchangeably, and describe Form 6 of sodium 4-{[9-chloro-7-(2-fluoro-6-methoxyphenyl)-5H-pyrimido[5,4-d][2]benzazepin-2-yl] amino}-2-methoxybenzoate, as synthesized in Example 5, in the Examples section below, and as described below, and represented by data shown in FIGS. 8, 9, 10, and 11.

"Form 11" or "sodium 4-{[9-chloro-7-(2-fluoro-6-methoxyphenyl)-5H-pyrimido[5,4-d][2]benzazepin-2-yl] amino}-2-methoxybenzoate Form 11" are used interchangeably, and describe describe Form 11 of sodium 4-{[9-chloro-7-(2-fluoro-6-methoxyphenyl)-5H-pyrimido[5,4-d][2] benzazepin-2-yl]amino}-2-methoxybenzoate, as synthesized in Example 6, in the Examples section below, and as described below, and represented by data shown in FIGS. 12 and 13.

"Form 12" or "sodium 4-{[9-chloro-7-(2-fluoro-6-methoxyphenyl)-5H-pyrimido[5,4-d][2]benzazepin-2-yl] amino}-2-methoxybenzoate Form 12" are used interchangeably, and describe Form 12 of sodium 4-{[9-chloro-7-(2-fluoro-6-methoxyphenyl)-5H-pyrimido[5,4-d][2] benzazepin-2-yl]amino}-2-methoxybenzoate, as synthesized in Example 7, in the Examples section below, and as described below, and represented by data shown in FIGS. 14, 15, and 16.

"Form 24" or "sodium 4-{[9-chloro-7-(2-fluoro-6-methoxyphenyl)-5H-pyrimido[5,4-d][2]benzazepin-2-yl] amino}-2-methoxybenzoate Form 24" are used interchangeably, and describe Form 24 of sodium 4-{[9-chloro-7-(2-fluoro-6-methoxyphenyl)-5H-pyrimido[5,4-d][2] benzazepin-2-yl]amino}-2-methoxybenzoate, as synthesized in Example 8, in the Examples section below, and as described below, and represented by data shown in FIGS. 17, 18, and 19.

As used herein, "crystalline" refers to a solid having a highly regular chemical structure. In particular, a crystalline Sodium Salt may be produced as one or more single crystalline forms of the Sodium Salt. For the purposes of this application, the terms "crystalline form", "single crystalline form" and "polymorph" are synonymous; the terms distinguish between crystals that have different properties (e.g., different XRPD patterns, different DSC scan results). The term "polymorph" includes pseudopolymorphs, which are typically different solvates of a material, and thus their properties differ from one another. Thus, each distinct polymorph and pseudopolymorph of the Sodium Salt is considered to be a distinct single crystalline form herein.

"Substantially crystalline" refers to Salts that may be at least a particular weight percent crystalline. Particular weight percentages are 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In some embodiments, substantially crystalline refers to Salts that are at least 70% crystalline. In other embodiments, substantially crystalline refers to Salts that are at least 90% crystalline.

The term "solvate or solvated" means a physical association of a compound of this invention with one or more solvent molecules. This physical association includes hydrogen bonding. In certain instances the solvate will be capable of isolation, for example when one or more solvent molecules are incorporated in the crystal lattice of the crystalline solid. "Solvate or solvated" encompasses both solution-phase and isolable solvates. Representative solvates include, for example, a hydrate, ethanolates or a methanolate.

The term "hydrate" is a solvate wherein the solvent molecule is $H_2O$ that is present in a defined stoichiometric amount, and may for example, include hemihydrate, monohydrate, dihydrate, or trihydrate.

The term "mixture" is used to refer to the combined elements of the mixture regardless of the phase-state of the combination (e.g., liquid or liquid/ crystalline).

The term "seeding" is used to refer to the addition of a crystalline material to initiate recrystallization or crystallization.

The term "antisolvent" is used to refer to a solvent in which compounds of the invention are poorly soluble.

A "subject" is preferably a bird or mammal, such as a human, but can also be an animal in need of veterinary treatment, e.g., domestic animals (e.g., dogs, cats, and the like), farm animals (e.g., cows, sheep, fowl, pigs, horses, and the like) and laboratory animals (e.g., rats, mice, guinea pigs, and the like).

"Treating" or "treatment" means prevention, partial alleviation, or cure of a disease, disorder or condition. The compounds and compositions of this invention are useful in treating mitotic kinase mediated diseases, disorders or conditions, particularly Aurora kinase mediated diseases, disorders or conditions. Inhibiting mitotic kinase activity may serve to treat a number of diseases, involving cell survival, proliferation, and migration, including cancer, as well as other cell-proliferative diseases.

As used herein, the term "Aurora kinase-mediated disorder" includes any disorder, disease or condition which is caused or characterized by an increase in Aurora kinase expression or activity, or which requires Aurora kinase activity. The term "Aurora kinase-mediated disorder" also includes any disorder, disease or condition in which inhibition of Aurora kinase activity is beneficial. Aurora kinase-mediated disorders include proliferative disorders. Non-limiting examples of proliferative disorders include chronic inflammatory proliferative disorders, e.g., psoriasis and rheumatoid arthritis; proliferative ocular disorders, e.g., diabetic retinopathy; benign proliferative disorders, e.g., hemangiomas; and cancer.

As used herein, the term "Aurora kinase" refers to any one of a family of related serine/threonine kinases involved in mitotic progression. A variety of cellular proteins that play a role in cell division are substrates for phosphorylation by Aurora kinase enzymes, including, without limitation, histone H3, p 53, CENP-A, myosin II regulatory light chain, protein phosphatase-1, TPX-2, INCENP, survivin, topoisomerase II alpha, vimentin, MBD-3, MgcRacGAP, desmin, Ajuba, XIEg5 (in *Xenopus*), Ndc10p (in budding yeast), and D-TACC (in *Drosophila*). Aurora kinase enzymes also are themselves substrates for autophosphorylation, e.g., at Thr288. Unless otherwise indicated by context, the term "Aurora kinase" is meant to refer to any Aurora kinase protein from any species, including, without limitation, Aurora A, Aurora B, and Aurora C, preferably Aurora A or B. Preferably, the Aurora kinase is a human Aurora kinase.

"Pharmaceutically effective amount" is meant to describe an amount of a compound, composition, medicament or other active ingredient effective in producing the desired therapeutic effect.

In one aspect, the present invention is directed to crystalline forms of sodium 4-{[9-chloro-7-(2-fluoro-6-methoxyphenyl)-5H-pyrimido[5,4-d][2]benzazepin-2-yl]amino}-2-methoxybenzoate of formula (I). Accordingly, the present invention provides solvates of sodium 4-{[9-chloro-7-(2-fluoro-6-methoxyphenyl)-5H-pyrimido [5,4-d][2]benzazepin-2-yl]amino}-2-methoxybenzoate of formula (I).

Provided herein is an assortment of characterizing information to describe the crystalline forms of sodium 4-{[9-chloro-7-(2-fluoro-6-methoxyphenyl)-5H-pyrimido[5,4-d] [2]benzazepin-2-yl]amino}-2-methoxybenzoate (I). It should be understood, however, that not all such information is required for one skilled in the art to determine that such particular form is present in a given composition, but that the determination of a particular form can be achieved using any portion of the characterizing information that one skilled in the art would recognize as sufficient for establishing the presence of a particular form, e.g., even a single distinguishing peak can be sufficient for one skilled in the art to appreciate that such particular form is present.

The Sodium Salt has properties that make it suitable for large scale pharmaceutical formulation manufacture. The crystalline forms of the Sodium Salt described herein exhibit increased aqueous solubility over the free acid compound of formula (II), which results in improved absorption of the active pharmaceutical ingredient. For example, in water the free acid has a solubility of about 10 μg/mL. In water, Form 2 has a solubility of about 8 mg/mL; Form 6 has a solubility of greater than about 10 mg/mL; and Form 24 has a solubility of about 8 mg/mL.

Embodiments of the invention are directed to the Sodium Salt, wherein at least a particular percentage by weight of the Sodium Salt is crystalline. In some embodiments, the Sodium Salt is substantially crystalline. Non-limiting examples of a crystalline Sodium Salt include a single crystalline form of the Sodium Salt or a mixture of different single crystalline forms. An embodiment of the invention is also directed to a Sodium Salt, wherein at least a particular percentage by weight of the Sodium Salt is crystalline, that excludes one or more designated single crystalline forms from a particular weight percentage of Sodium Salt. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. When a particular percentage by weight of the Sodium Salt is crystalline, the remainder of the Sodium Salt is the amorphous form of the Sodium Salt.

Alternatively, embodiments of the invention are directed to a crystalline Sodium Salt, wherein at least a particular percentage by weight of the crystalline Sodium Salt is a specific single crystalline form, a combination of particular crystalline forms, or excludes one or more particular crystalline forms. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%.

Other embodiments of the invention are directed to the Sodium Salt being a single crystalline form, or being substantially a designated single crystalline form. The single crystalline form may be a particular percentage by weight of the Sodium Salt. Particular weight percentages are 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. When a particular percentage by weight of a Sodium Salt is a single crystalline form, the remainder of the Sodium Salt is some combination of amorphous form of the Sodium Salt, and one or more crystalline forms of the Sodium Salt excluding the single crystalline form. In some embodiments, the Sodium Salt is at least 90% by weight of a single crystalline form. In some other embodiments, the Sodium Salt is at least 95% by weight of a single crystalline form.

In the following description of the Sodium Salt, embodiments of the invention may be described with reference to a particular crystalline form of the Sodium Salt, as characterized by one or more properties as discussed herein. The descriptions characterizing the crystalline forms may also be used to describe the mixture of different crystalline forms that may be present in a crystalline Sodium Salt. However, the particular crystalline forms of the Sodium Salt may also be characterized by one or more of the characteristics of the crystalline form as described herein, with or without regard to referencing a particular crystalline form.

The processes and compounds of the present invention are further illustrated by the detailed descriptions and illustrative examples given below.

Form 1

In one embodiment of the invention, a single crystalline form, Form 1, of the Sodium Salt is characterized by the X-ray powder diffraction (XRPD) pattern shown in FIG. 1, and data shown in Table 1, obtained using CuKα radiation. In a particular embodiment of the invention, the polymorph can be characterized by one or more of the peaks taken from FIG. 1, as shown in Table 1.

TABLE 1

| Angle 2-Theta ° | Intensity % |
|---|---|
| 4.44 | 13.7 |
| 8.77 | 63.1 |
| 9.40 | 18.6 |
| 10.23 | 100 |
| 10.91 | 43.2 |
| 11.71 | 20.5 |
| 12.23 | 26.7 |

TABLE 1-continued

| Angle 2-Theta ° | Intensity % |
|---|---|
| 13.32 | 26.4 |
| 14.14 | 40.8 |
| 14.94 | 81.1 |
| 15.46 | 35.6 |
| 17.98 | 56.7 |
| 18.94 | 48.6 |
| 20.30 | 42.9 |
| 21.35 | 65.0 |
| 22.64 | 89.7 |
| 23.97 | 74.3 |
| 24.71 | 62.0 |
| 25.67 | 73.5 |
| 26.53 | 68.8 |
| 28.89 | 61.8 |

In another embodiment of the invention, the peaks are identified at 2θ angles of 8.77°, 10.23°, 14.94°, 21.35°, 22.64°, 23.97°, and 25.67°. In a further particular embodiment, the peaks are identified at 2θ angles of 10.23°, 14.94°, 22.64°, 23.97°, and 25.67°. In a further particular, embodiment, the peaks are identified at 2θ angles of 10.23°, 14.94°, and 22.64°.

Figure 2:
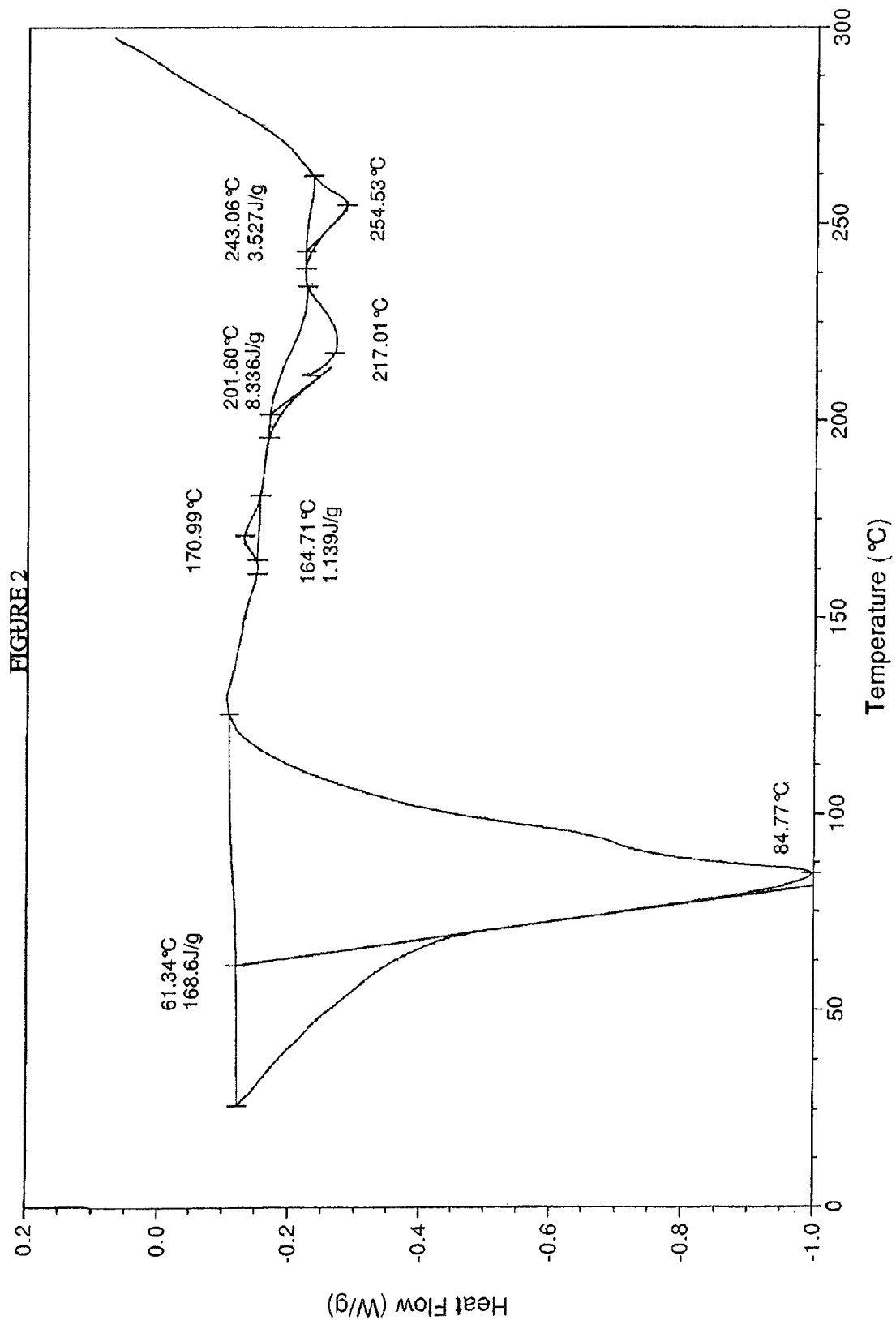
FIG. 2 is a differential scanning calorimetry (DSC) profile for sodium 4-{[9-chloro-7-(2-fluoro-6-methoxyphenyl)-5H-pyrimido [5,4-d][2]benzazepin-2-yl]amino}-2-methoxybenzoate Form 1.

In another embodiment of the invention, Form 1 can be characterized by the differential scanning calorimetry profile (DSC) shown in FIG. 2. The DSC graph plots the heat flow as a function of temperature from a sample, the temperature rate change being about 10° C./min. The profile is characterized by exothermic and endothermic transitions. The first is a strong endothermic transition with an onset temperature of about 61° C. with a melt at about 85° C., which is followed by a weak exothermic transition with an onset temperature of about 165°C. The third and fourth endothermic transitions are both weak with onset temperatures of about 202° C. and about 243° C., respectively. These temperatures have an error of ±2° C.

Figure 3:
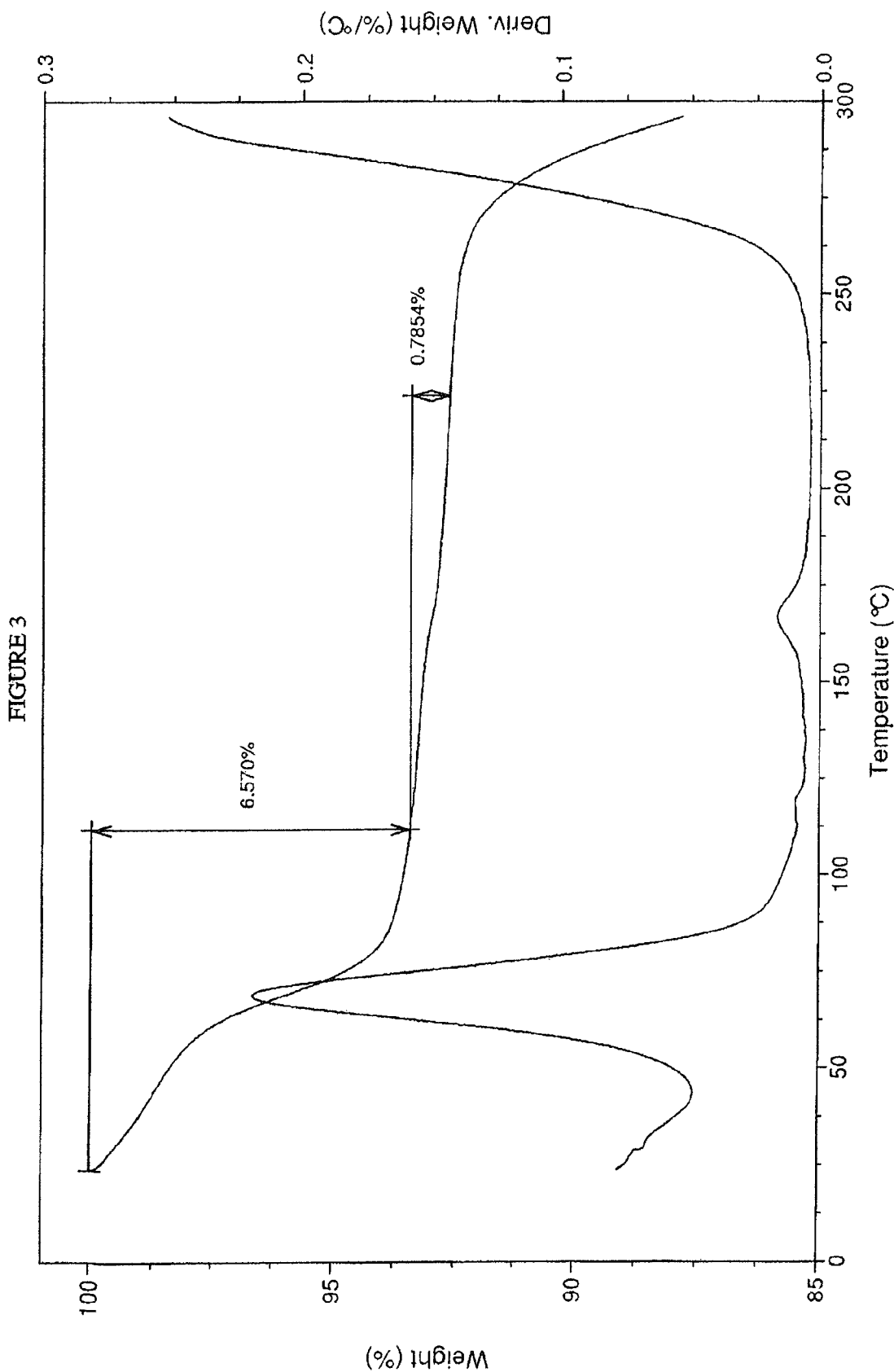
FIG. 3 is a thermal gravimetric analysis (TGA) profile for sodium 4-{[9-chloro-7-(2-fluoro-6-methoxyphenyl)-5H-pyrimido[5,4-d][2]benzazepin-2-yl]amino}-2-methoxybenzoate Form 1.

In another embodiment of the invention, Form 1 can be characterized by thermal gravimetric analysis (TGA) shown in FIG. 3. The TGA profile graphs the percent loss of weight of the sample as a function of temperature, the temperature rate change being about 10° C./min. The weight loss represents a loss of about 7.4% of the weight of the sample as the temperature is changed from 25° C. to 250° C.

In another embodiment of the invention, Form 1 is characterized by at least one of the following features (I-i)-(I-iv):
(I-i) at least one of the X-ray powder diffraction peaks shown in Table 1;
(I-ii) an X-ray powder diffraction pattern substantially similar to FIG. 1;
(I-iii) a differential scanning calorimetry (DSC) profile substantially similar to FIG. 2; and
(I-iv) a thermal gravimetric analysis (TGA) profile substantially similar to FIG. 3.

In a further embodiment of the invention, a single crystalline form of Form 1 is characterized by two of the features (I-i)-(I-iv). In a further embodiment of the invention, a single crystalline form of Form 1 is characterized by three of the features (I-i)-(I-iv). In a further embodiment of the invention, a single crystalline form of Form 1 is characterized by all of the features (I-i)-(I-iv).

Form 2

Figure 4:
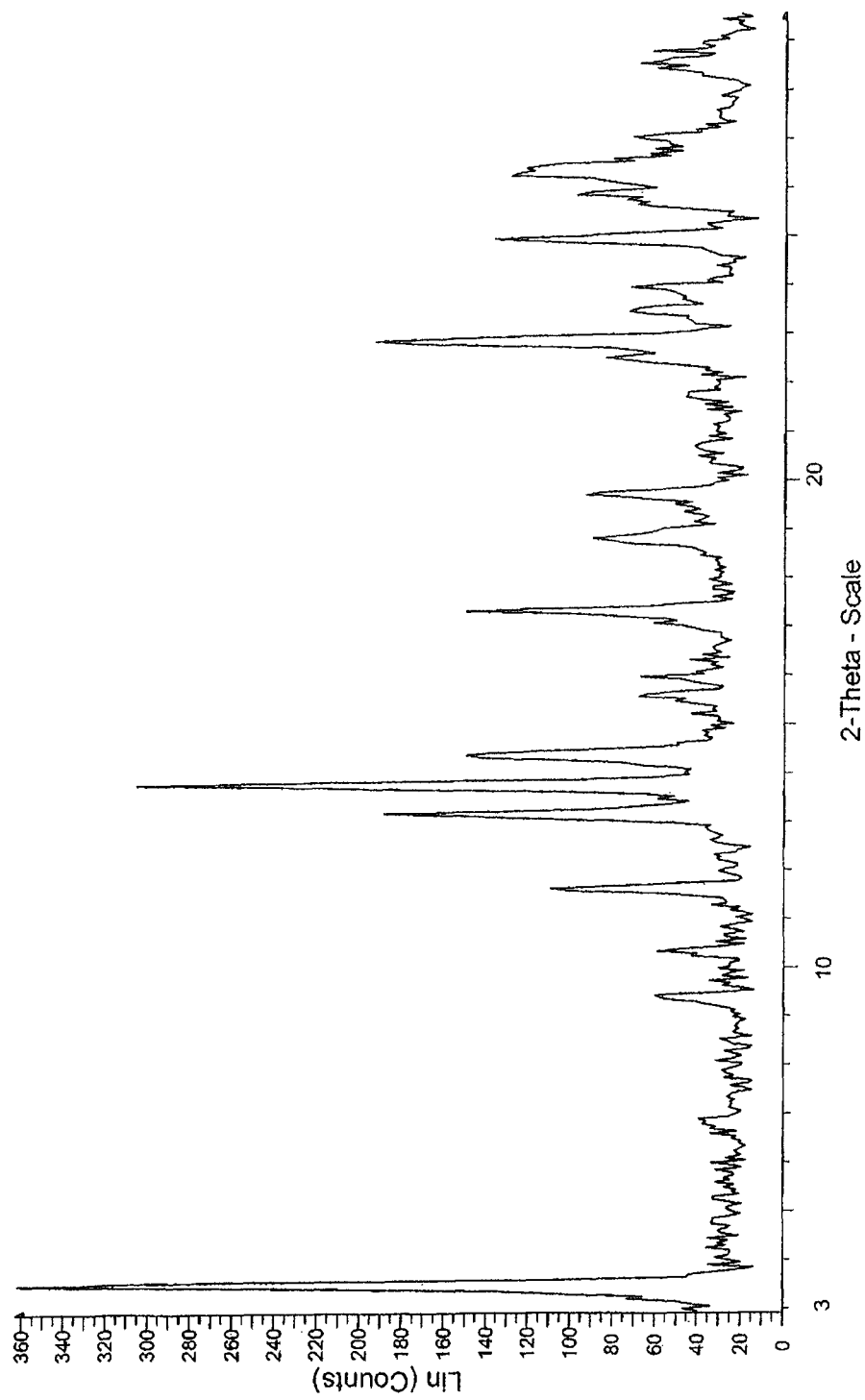
FIG. 4 is a powder X-ray diffractogram (XRPD) of sodium 4-{[9-chloro-7-(2-fluoro-6-methoxyphenyl)-5H-pyrimido [5,4-d][2]benzazepin-2-yl]amino}-2-methoxybenzoate Form 2.

In one embodiment of the invention, a single crystalline form, Form 2, of the Sodium Salt is characterized by the X-ray powder diffraction (XRPD) pattern shown in FIG. 4, and data shown in Table 2, obtained using CuKα radiation. In a particular embodiment of the invention, the polymorph can be characterized by one or more of the peaks taken from FIG. 4, as shown in Table 2.

TABLE 2

| Angle 2-Theta ° | Intensity % |
|---|---|
| 3.44 | 100 |
| 4.76 | 9.1 |
| 6.80 | 10.7 |
| 7.80 | 7.7 |
| 9.36 | 16.5 |
| 10.29 | 16.3 |
| 11.58 | 30.3 |
| 11.96 | 8.3 |
| 12.24 | 8.8 |
| 13.11 | 52.1 |
| 13.73 | 84.3 |
| 14.36 | 41.3 |
| 15.59 | 18.7 |
| 15.92 | 18.5 |
| 17.31 | 41.3 |
| 18.77 | 24.8 |
| 19.72 | 25.6 |
| 21.71 | 12.7 |
| 22.48 | 23.1 |
| 22.84 | 53.2 |
| 23.51 | 20.1 |
| 23.91 | 19.8 |
| 24.92 | 37.7 |
| 25.65 | 19.0 |
| 25.91 | 27.0 |
| 26.39 | 33.6 |
| 27.00 | 19.6 |
| 28.57 | 18.7 |

In another embodiment of the invention, the peaks are identified at 2θ angles of 3.44°, 13.11°, 13.73°, 14.36°, 17.31°, and 22.84°. In a further particular embodiment, the peaks are identified at 2θ angles of 3.44°, 13.11°, 13.73°, and 22.84°.

Figure 5:
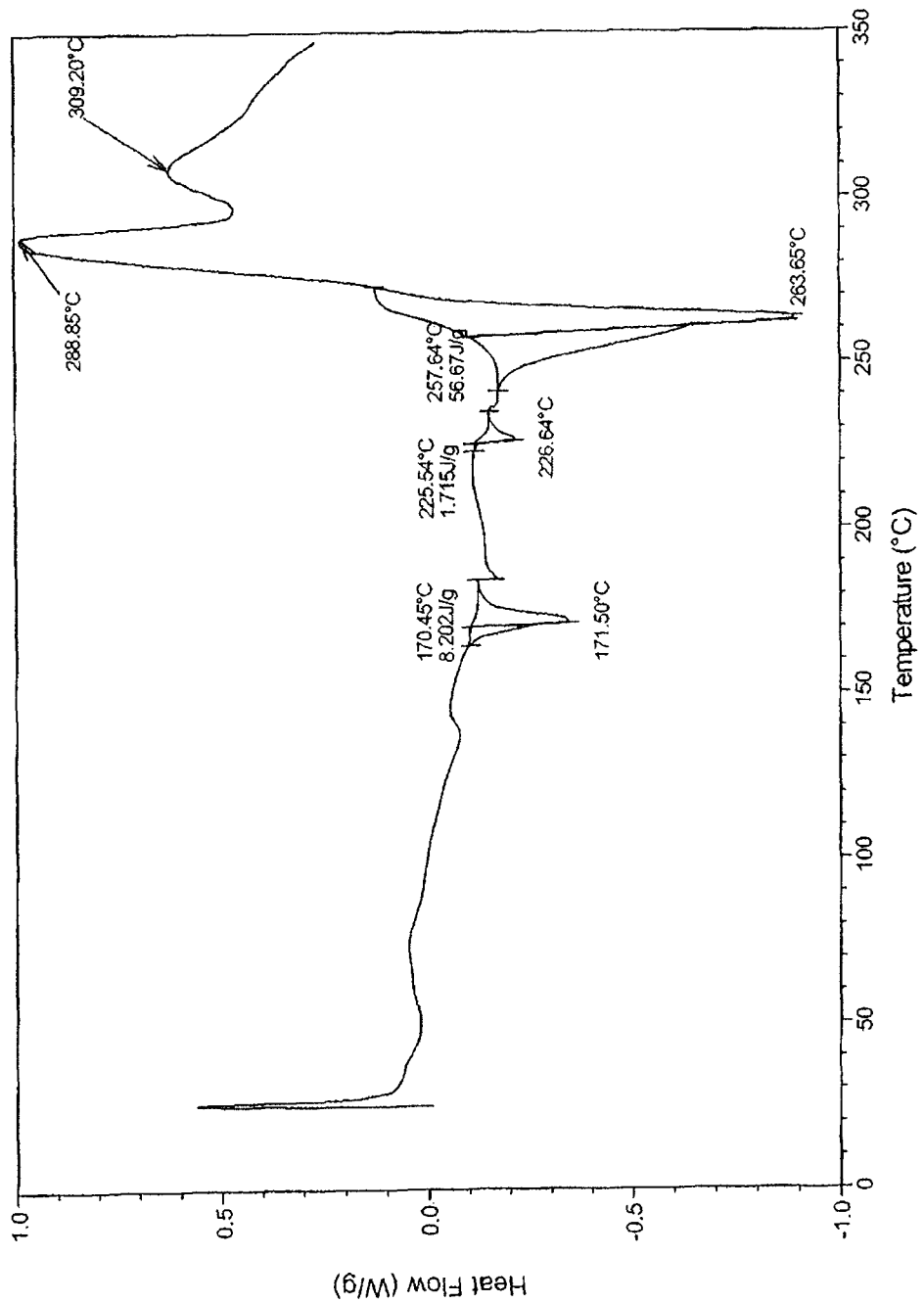
FIG. 5 is a differential scanning calorimetry (DSC) profile for sodium 4-{[9-chloro-7-(2-fluoro-6-methoxyphenyl)-5H-pyrimido [5,4-d][2]benzazepin-2-yl]amino}-2-methoxybenzoate Form 2.

In another embodiment of the invention, Form 2 can be characterized by the differential scanning calorimetry profile (DSC) shown in FIG. 5. The DSC graph plots the heat flow as a function of temperature from a sample, the temperature rate change being about 10° C./min. The profile is characterized by exothermic and endothermic transitions. The first and second endothermic transitions have an onset temperature of about 171° C. and about 226° C., respectively. The third transition is a strong endothermic transition with an onset temperature of about 258° C. with a melt at about 264° C. This transition is followed by two exothermic transitions at about 289° C. and at about 309° C. These temperatures have an error of ±2° C.

Figure 6:
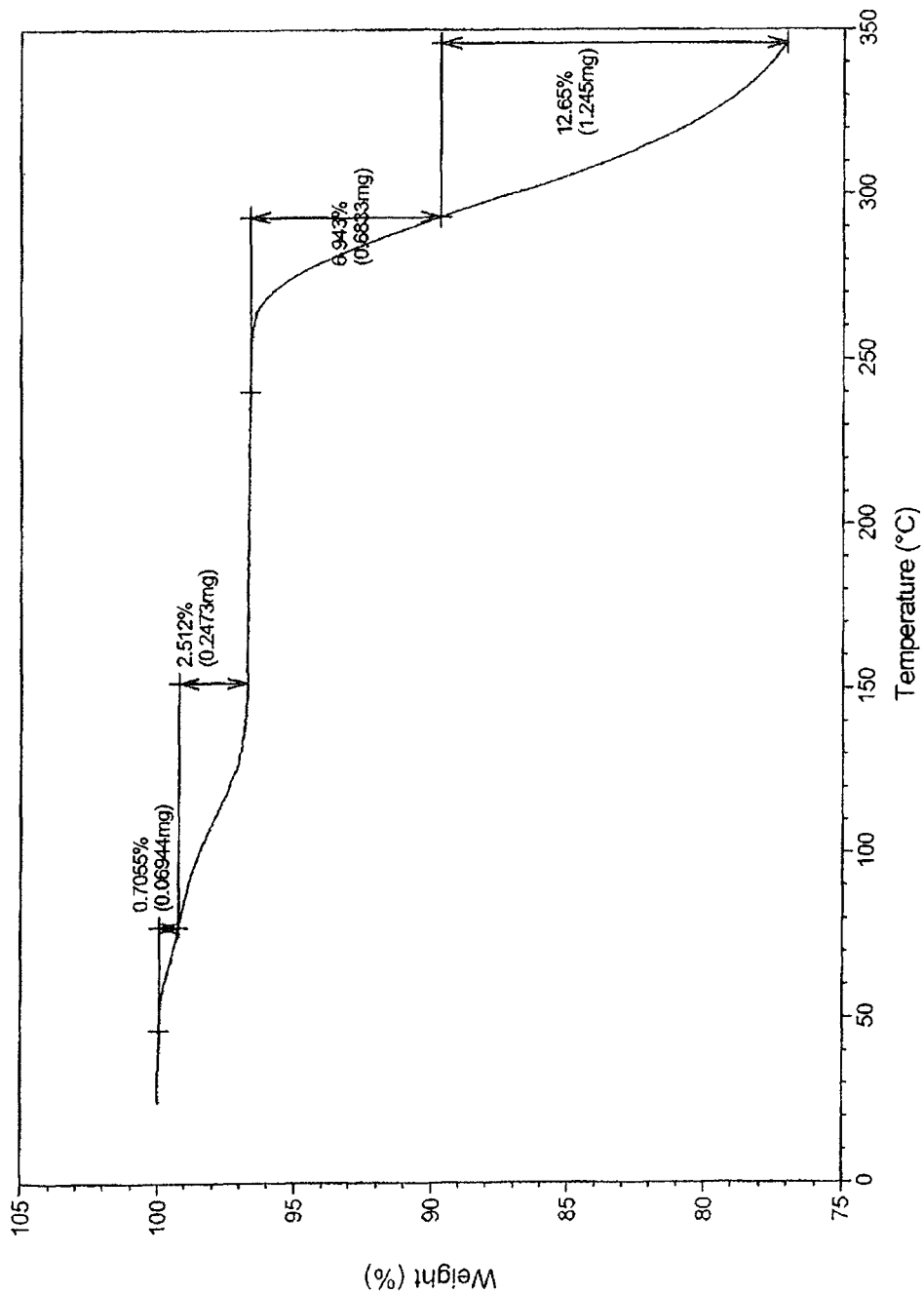
FIG. 6 is a thermal gravimetric analysis (TGA) profile for sodium 4-{[9-chloro-7-(2-fluoro-6-methoxyphenyl)-5H-pyrimido[5,4-d][2]benzazepin-2-yl]amino}-2-methoxybenzoate Form 2.

In another embodiment of the invention, Form 2 can be characterized by thermal gravimetric analysis (TGA) shown in FIG. 6. The TGA profile graphs the percent loss of weight of the sample as a function of temperature, the temperature rate change being about 10° C./min. The weight loss represents a loss of about 22.8% of the weight of the sample as the temperature is changed from 25° C. to 350° C.

In another embodiment of the invention, Form 2 is characterized by at least one of the following features (II-i)-(II-iv):
(II-i) at least one of the X-ray powder diffraction peaks shown in Table 2;
(II-ii) an X-ray powder diffraction pattern substantially similar to FIG. 4;
(II-iii) a differential scanning calorimetry (DSC) profile substantially similar to FIG. 5; and
(II-iv) a thermal gravimetric analysis (TGA) profile substantially similar to FIG. 6.

In a further embodiment of the invention, a single crystalline form of Form 2 is characterized by two of the features (II-i)-(II-iv). In a further embodiment of the invention, a single crystalline form of Form 2 is characterized by three of the features (II-i)-(II-iv). In a further embodiment of the invention, a single crystalline form of Form 2 is characterized by all of the features (II-i)-(II-iv).

Form 4

Figure 7:
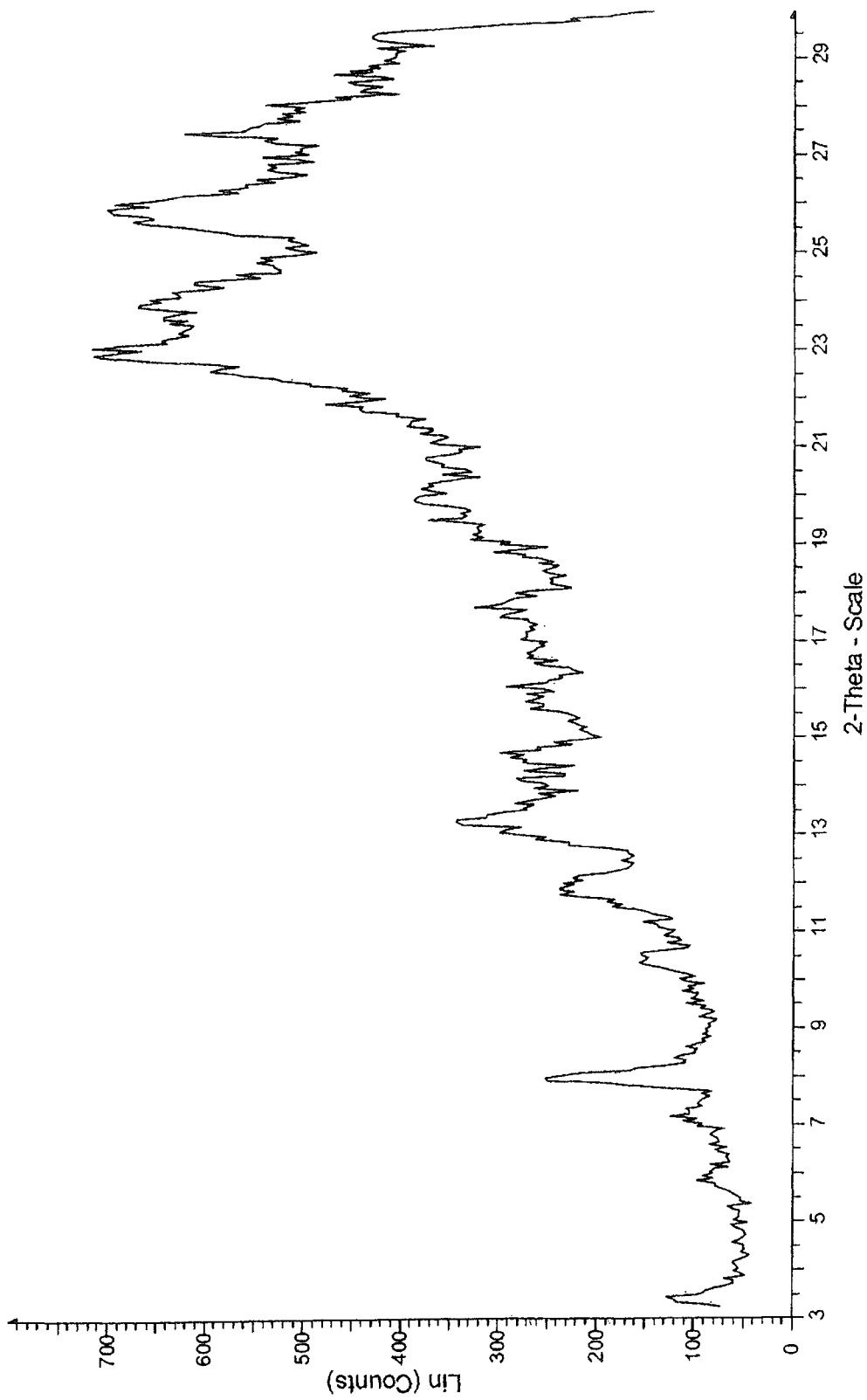
FIG. 7 is a powder X-ray diffractogram (XRPD) of sodium 4-{[9-chloro-7-(2-fluoro-6-methoxyphenyl)-5H-pyrimido [5,4-d][2]benzazepin-2-yl]amino}-2-methoxybenzoate Form 4.

In one embodiment of the invention, a single crystalline form, Form 4, of the Sodium Salt is characterized by the X-ray powder diffraction (XRPD) pattern shown in FIG. 7, and data shown in Table 3, obtained using CuKα radiation. In a particular embodiment of the invention, the polymorph can be characterized by one or more of the peaks taken from FIG. 7.

TABLE 3

| Angle 2-Theta ° | Intensity % |
|---|---|
| 3.42 | 17.7 |
| 7.95 | 34.9 |
| 13.27 | 48.2 |
| 22.96 | 100 |
| 25.89 | 98.8 |

In another embodiment of the invention, the peaks are identified at 2θ angles of 13.27°, 22.96°, and 25.89°. In a further particular embodiment, the peaks are identified at 2θ angles of 22.96° and 25.89°.

In another embodiment of the invention, Form 4 is characterized by at least one of the following features (III-i)-(III-ii):
(III-i) at least one of the X-ray powder diffraction peaks shown in Table 3; and
(III-ii) an X-ray powder diffraction pattern substantially similar to FIG. 7.

In a further embodiment of the invention, a single crystalline form of Form 4 is characterized by both of the features (III-i)-(III-ii).

Form 6

Figure 8:
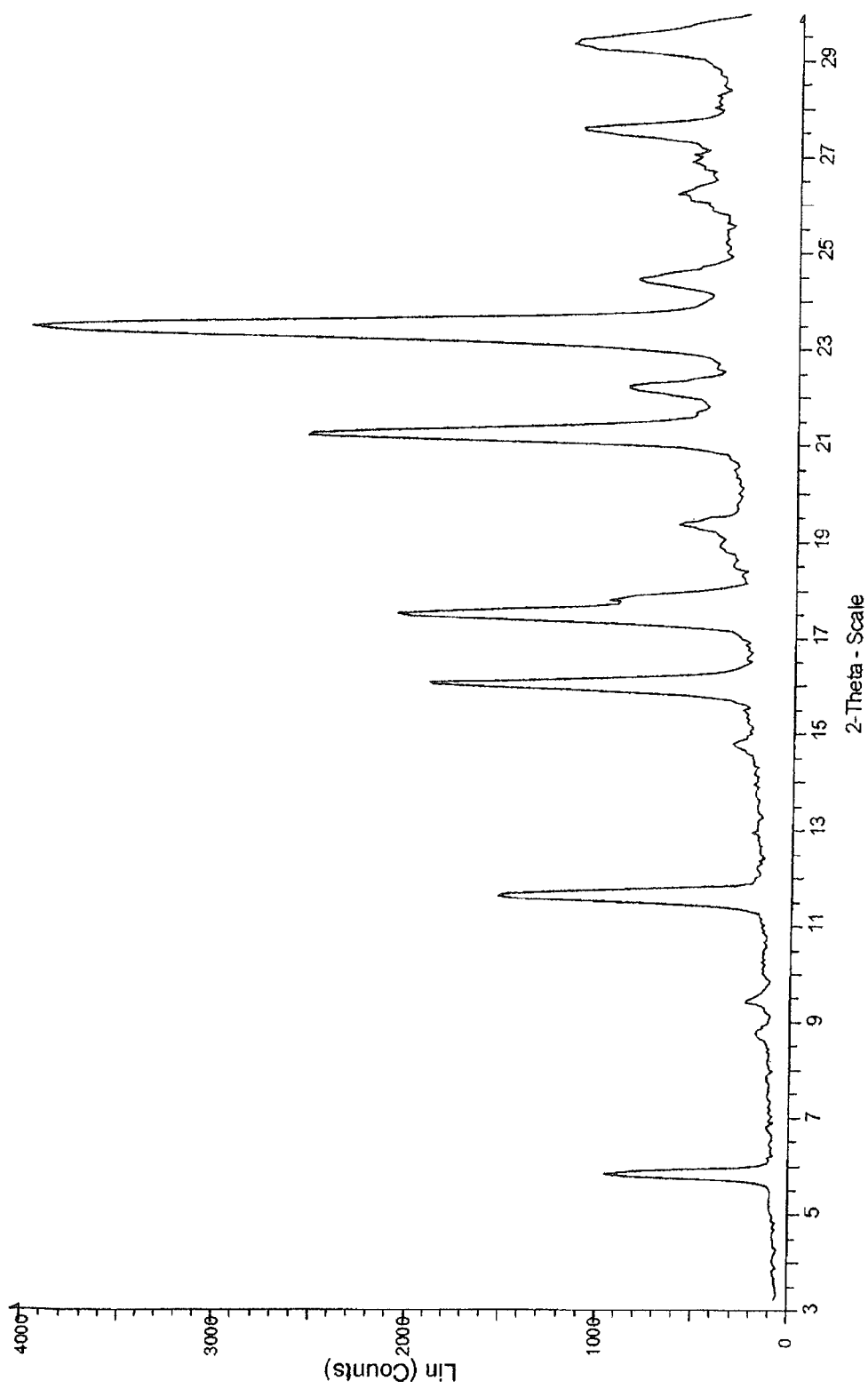
FIG. 8 is a powder X-ray diffractogram (XRPD) of sodium 4-{[9-chloro-7-(2-fluoro-6-methoxyphenyl)-5H-pyrimido [5,4-d][2]benzazepin-2-yl]amino}-2-methoxybenzoate Form 6.

In one embodiment of the invention, a single crystalline form, Form 6, of the Sodium Salt is characterized by the X-ray powder diffraction (XRPD) pattern shown in FIG. 8, and data shown in Table 4, obtained using CuKα radiation. In a particular embodiment of the invention, the polymorph can be characterized by one or more of the peaks taken from FIG. 8.

TABLE 4

| Angle 2-Theta ° | Intensity % |
|---|---|
| 5.81 | 23.8 |
| 9.42 | 5.6 |
| 11.62 | 38.0 |
| 14.78 | 7.8 |
| 16.01 | 47.6 |
| 17.47 | 51.9 |
| 17.80 | 24.4 |
| 19.38 | 15.2 |
| 21.23 | 63.8 |
| 22.21 | 21.8 |
| 23.43 | 100 |
| 24.47 | 20.8 |
| 26.23 | 15.8 |
| 27.57 | 28.1 |
| 29.38 | 29.6 |

In another embodiment of the invention, the peaks are identified at 2θ angles of 11.62°, 16.01°, 17.47°, 21.23°, 23.43°, and 29.38°. In a further particular embodiment, the peaks are identified at 2θ angles of 16.01°, 17.47°, 21.23°, and 23.43°.

Figure 9:
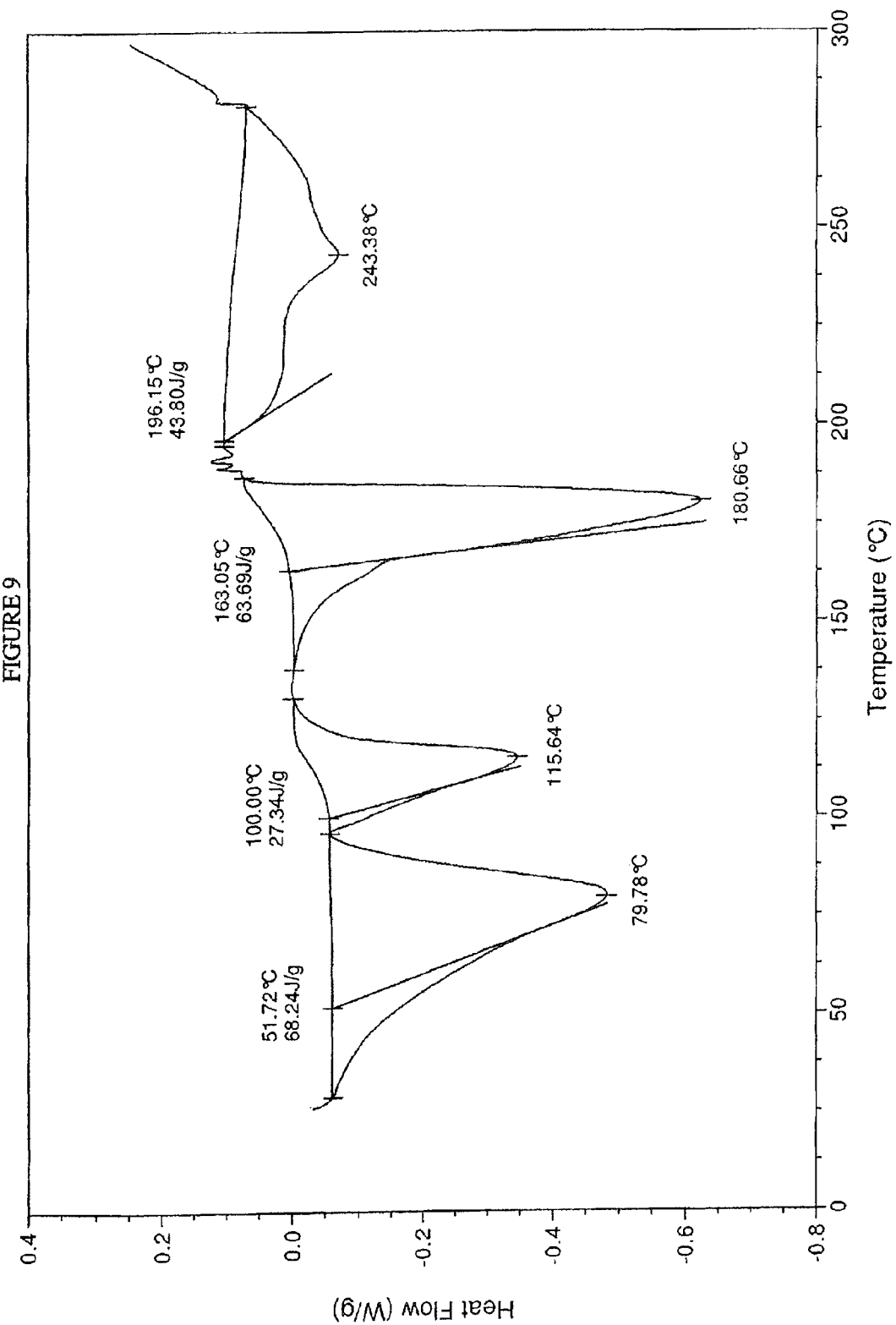
FIG. 9 is a differential scanning calorimetry (DSC) profile for sodium 4-{[9-chloro-7-(2-fluoro-6-methoxyphenyl)-5H-pyrimido[5,4-d][2]benzazepin-2-yl]amino}-2-methoxybenzoate Form 6.

In another embodiment of the invention, Form 6 can be characterized by the differential scanning calorimetry profile (DSC) shown in FIG. 9. The DSC graph plots the heat flow as a function of temperature from a sample, the temperature rate change being about 10° C./min. The profile is characterized by endothermic transitions. The first endothermic transition has an onset temperature of about 52° C. This is followed by an endothermic transition with an onset temperature of about 100° C. The next endothermic transition has an onset temperature of about 163° C. with a melt at about 181° C. The final endothermic transition has an onset temperature of about 196° C. These temperatures have an error of ±2° C.

Figure 10:
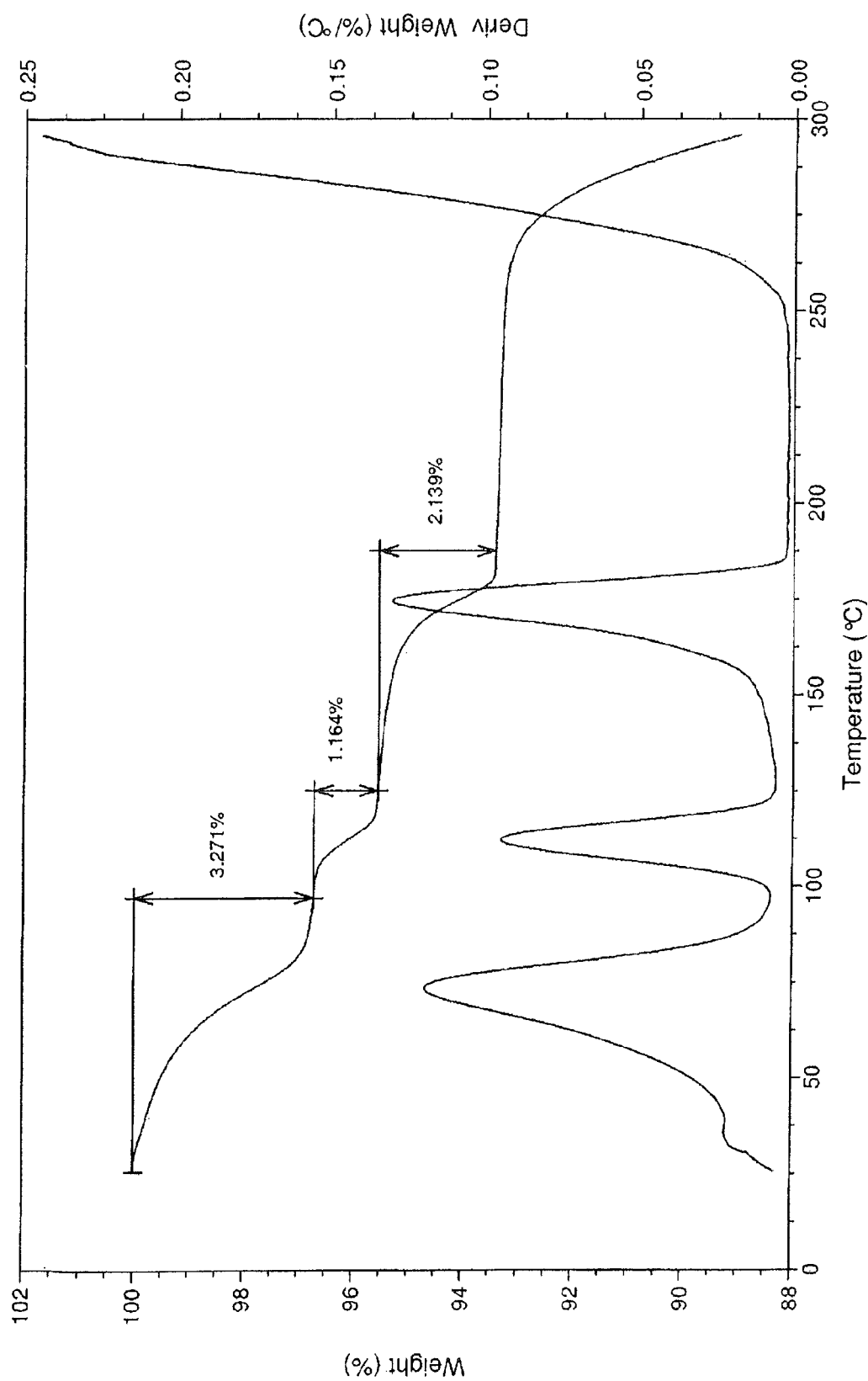
FIG. 10 is a thermal gravimetric analysis (TGA) profile for sodium 4-{[9-chloro-7-(2-fluoro-6-methoxyphenyl)-5H-pyrimido[5,4-d][2]benzazepin-2-yl]amino}-2-methoxybenzoate Form 6.

In another embodiment of the invention, Form 6 can be characterized by the thermal gravimetric analysis (TGA) shown in FIG. 10, which graphs the percent loss of weight of the sample as a function of temperature, the temperature rate change being about 10° C./min. The weight loss represents a loss of about 6.6% of the weight of the sample as the temperature is changed from 25° C. to about 200° C.

Figure 11:
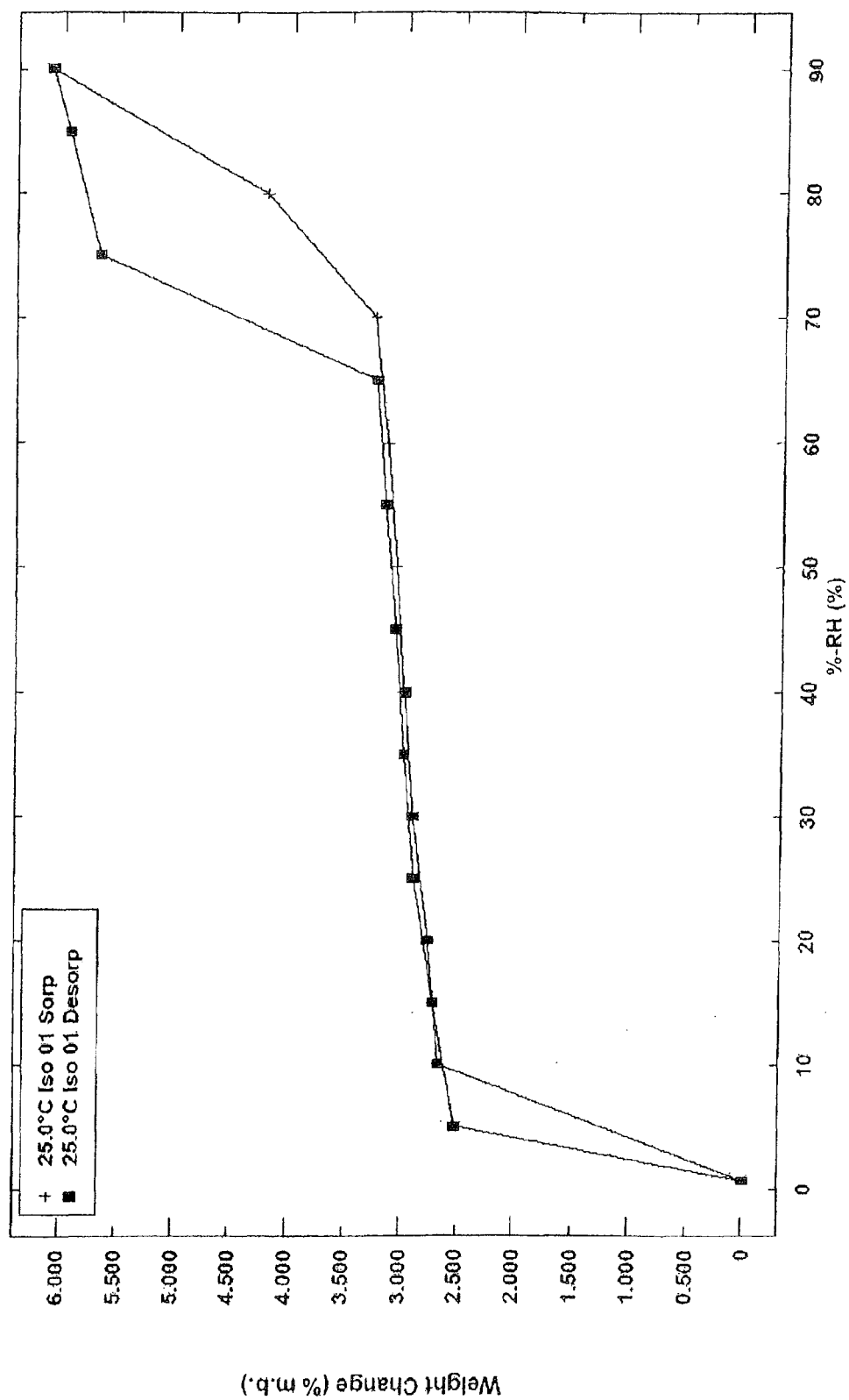
FIG. 11 is a gravimetric vapor sorption (GVS) profile of sodium 4-{[9-chloro-7-(2-fluoro-6-methoxyphenyl)-5H-pyrimido [5,4-d][2]benzazepin-2-yl]amino}-2-methoxybenzoate Form 6.

In another embodiment of the invention, Form 6, can be characterized by the vapor sorption profiles (GVS), as shown in FIG. 11. The profile shows the change in weight of the sample as the relative humidity (RH) of the environment is changed by 10% RH intervals over a 0-90% RH range at a temperature of 25° C. Form 6 showed a 6% uptake between 0-90% RH.

In another embodiment of the invention, Form 6 is characterized by at least one of the following features (IV-i)-(IV-v):
 (IV-i) at least one of the X-ray powder diffraction peaks shown in Table 4;
 (IV-ii) an X-ray powder diffraction pattern substantially similar to FIG. 8;
 (IV-iii) a differential scanning calorimetry (DSC) profile substantially similar to FIG. 9;
 (IV-iv) a thermal gravimetric analysis (TGA) substantially similar to FIG. 10; and
 (IV-v) a gravimetric vapor sorption (GVS) profile substantially similar to FIG. 11.

In a further embodiment of the invention, a single crystalline form of Form 6 is characterized by two of the features (IV-i)-(IV-v). In a further embodiment of the invention, a single crystalline form of Form 6 is characterized by three of the features (IV-i)-(IV-v). In a further embodiment of the invention, a single crystalline form of Form 6 is characterized by four of the features (IV-i)-(IV-v). In a further embodiment of the invention, a single crystalline form of Form 6 is characterized by all of the features (IV-i)-(IV-v).

Form 11

Figure 12:
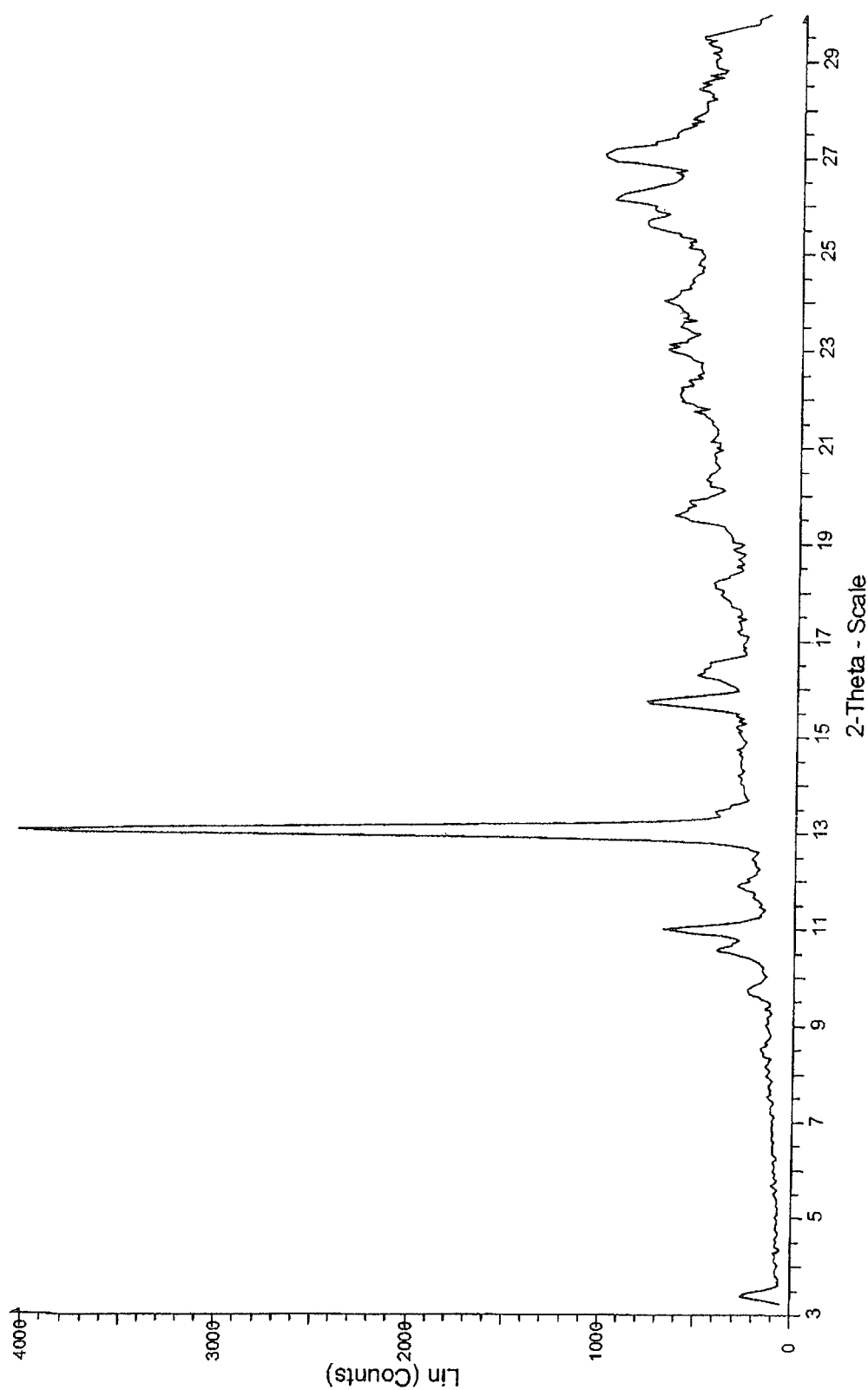
FIG. 12 is a powder X-ray diffractogram (XRPD) of sodium 4-{[9-chloro-7-(2-fluoro-6-methoxyphenyl)-5H-pyrimido[5,4-d][2]benzazepin-2-yl]amino}-2-methoxybenzoate Form 11.

In one embodiment of the invention, a single crystalline form, Form 11, of the Sodium Salt is characterized by the X-ray powder diffraction (XRPD) pattern shown in FIG. 12, and data shown in Table 5, obtained using CuKα radiation. In a particular embodiment of the invention, the polymorph can be characterized by one or more of the peaks taken from FIG. 12.

TABLE 5

| Angle 2-Theta ° | Intensity % |
| --- | --- |
| 3.37 | 6.5 |
| 9.73 | 5.7 |
| 10.60 | 9.7 |
| 10.96 | 16.6 |
| 11.91 | 7.1 |
| 13.03 | 100 |
| 13.44 | 10.6 |
| 15.72 | 19.1 |
| 16.32 | 12.7 |
| 19.62 | 15.8 |
| 25.66 | 19.7 |
| 26.21 | 24.0 |
| 27.08 | 25.4 |

In another embodiment of the invention, the peaks are identified at 2θ angles of 13.03°, 15.72°, 25.66°, 26.21°, and 27.08°. In a further particular embodiment, the peaks are identified at 2θ angles of 13.03°, 26.21°, and 27.08°.

Figure 13:
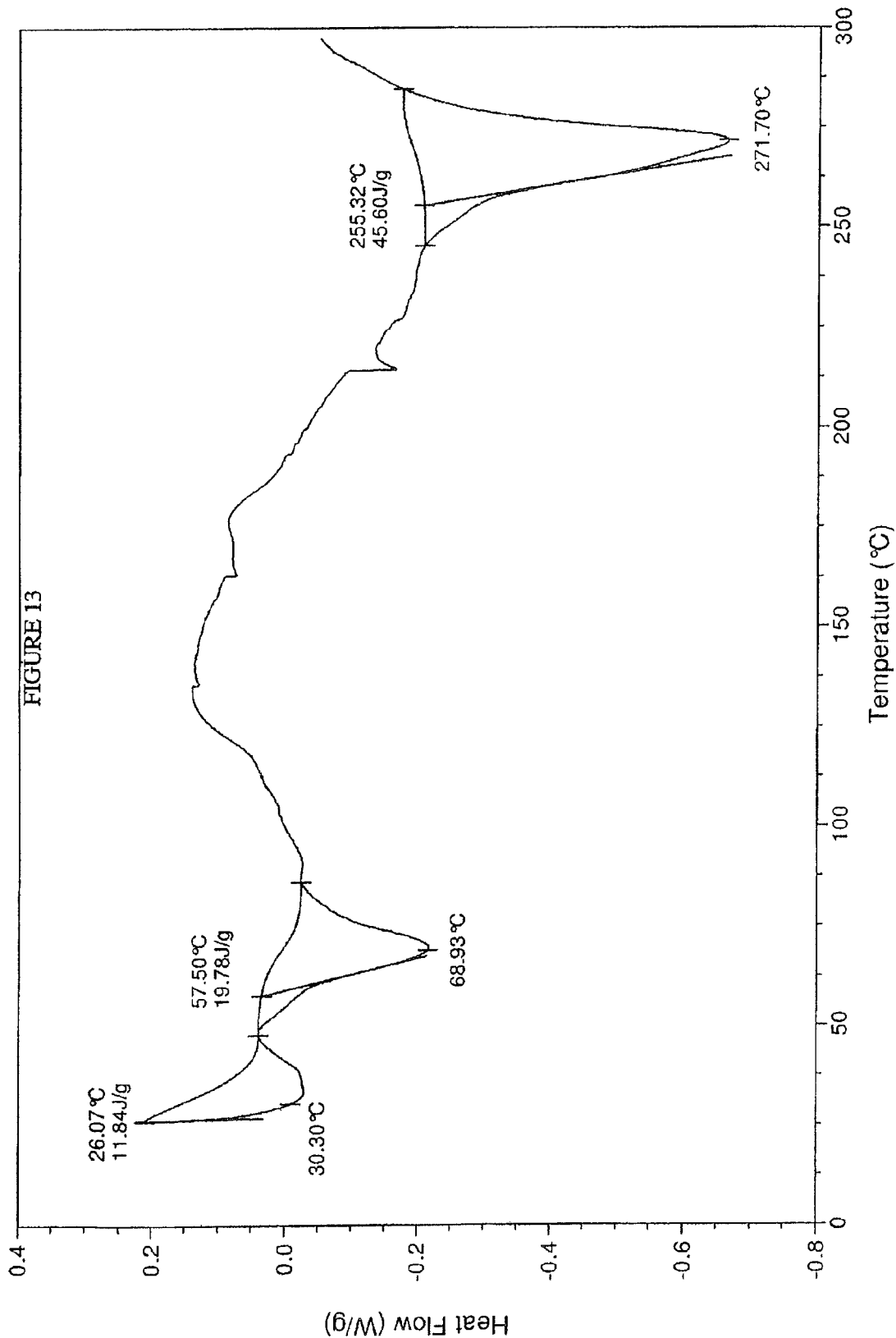
FIG. 13 is a differential scanning calorimetry (DSC) profile for sodium 4-{[9-chloro-7-(2-fluoro-6-methoxyphenyl)-5H-pyrimido [5,4-d][2]benzazepin-2-yl]amino}-2-methoxybenzoate Form 11.

In another embodiment of the invention, Form 11 can be characterized by the differential scanning calorimetry profile (DSC) shown in FIG. 13. The DSC graph plots the heat flow as a function of temperature from a sample, the temperature rate change being about 10° C./min. The profile is characterized by endothermic transitions. The first is an endothermic transition with an onset temperature of about 26° C. The second endothermic transition has an onset temperature of about 58° C. The third endothermic transition has an onset temperature of about 255° C., with a melt at about 272° C. These temperatures have an error of ±2° C.

In another embodiment of the invention, Form 11 is characterized by at least one of the following features (V-i)-(V-iii):
 (V-i) at least one of the X-ray powder diffraction peaks shown in Table 5;
 (V-ii) an X-ray powder diffraction pattern substantially similar to FIG. 12; and
 (V-iii) a differential scanning calorimetry (DSC) profile substantially similar to FIG. 13.

In a further embodiment of the invention, a single crystalline form of Form 11 is characterized by two of the features (V-i)-(V-iii). In another further embodiment of the invention, a single crystalline form of Form 11 is characterized by all of the features (V-i)-(V-iii).

Form 12

Figure 14:
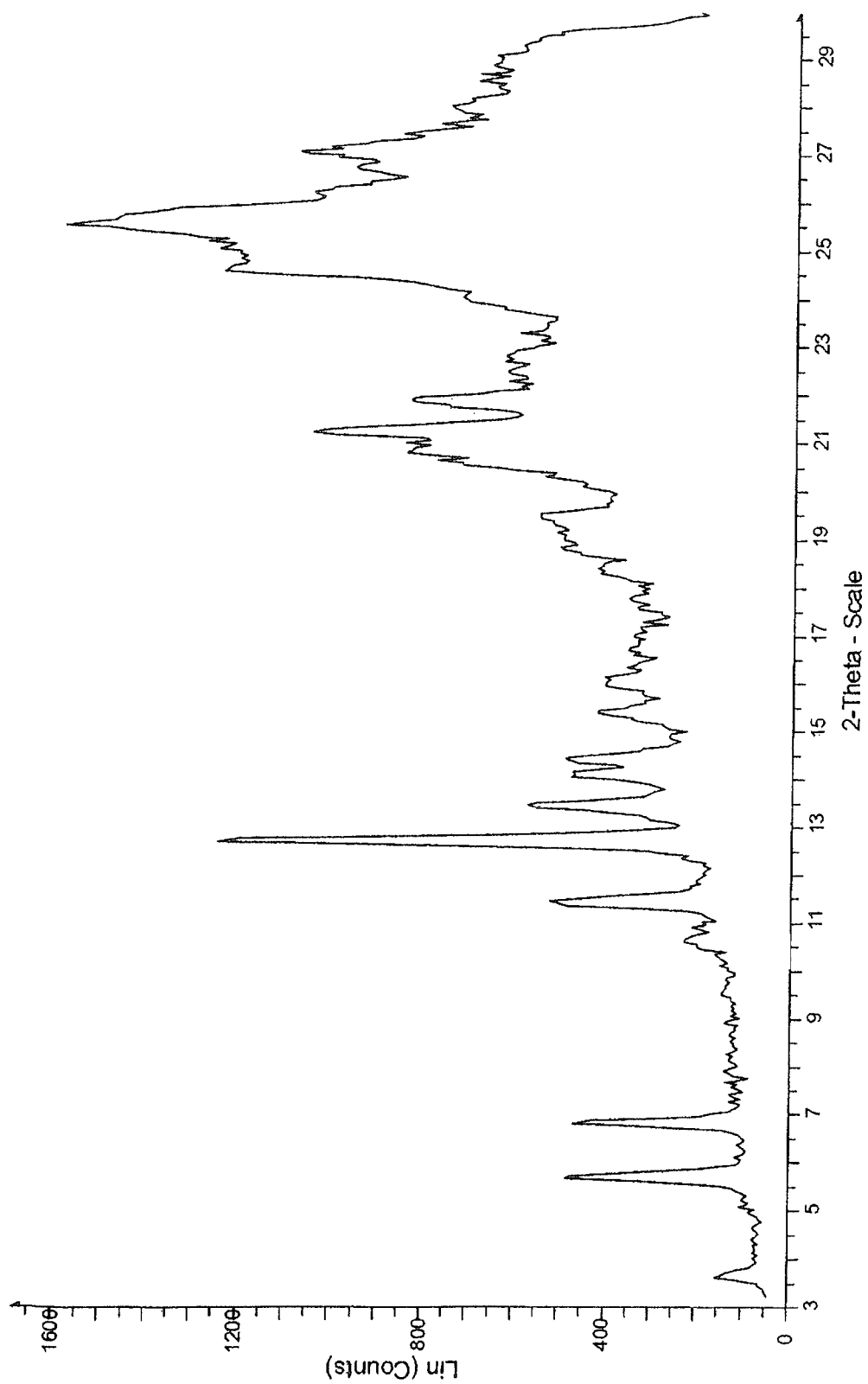
FIG. 14 is a powder X-ray diffractogram (XRPD) of sodium 4-{[9-chloro-7-(2-fluoro-6-methoxyphenyl)-5H-pyrimido[5,4-d][2]benzazepin-2-yl]amino}-2-methoxybenzoate Form 12.

In one embodiment of the invention, a single crystalline form, Form 12, of the Sodium Salt is characterized by the X-ray powder diffraction (XRPD) pattern shown in FIG. 14, and data shown in Table 6, obtained using CuKα radiation. In a particular embodiment of the invention, the polymorph can be characterized by one or more of the peaks taken from FIG. 14.

TABLE 6

| Angle 2-Theta ° | Intensity % |
| --- | --- |
| 3.63 | 9.5 |
| 5.67 | 30.4 |
| 6.83 | 29.2 |
| 11.42 | 32.7 |
| 12.72 | 78.5 |
| 13.46 | 35.8 |
| 14.11 | 29.9 |
| 14.40 | 30.8 |
| 15.39 | 27.0 |
| 21.26 | 66.0 |
| 21.89 | 52.6 |

TABLE 6-continued

| Angle 2-Theta ° | Intensity % |
|---|---|
| 25.57 | 100 |
| 29.50 | 35.8 |

In another embodiment of the invention, the peaks are identified at 2θ angles of 12.72°, 13.46°, 21.26°, 21.89°, 25.57°, and 29.50°. In a further particular embodiment, the identified at 2θ angles of 12.72°, 21.26°, 21.89°, and 25.57°.

Figure 15:
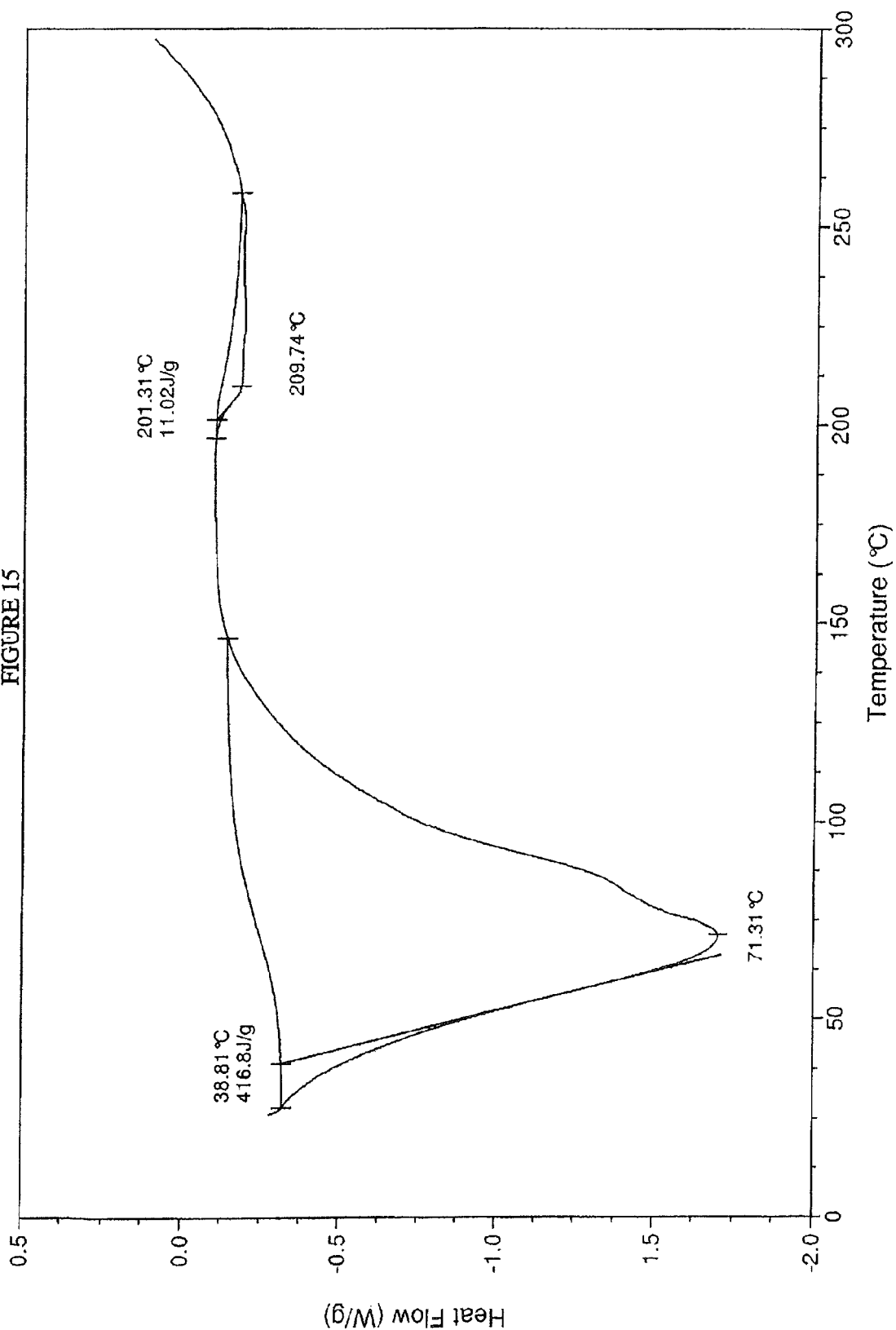
FIG. 15 is a differential scanning calorimetry (DSC) profile for sodium 4-{[9-chloro-7-(2-fluoro-6-methoxyphenyl)-5H-pyrimido [5,4-d][2]benzazepin-2-yl]amino}-2-methoxybenzoate Form 12.

In another embodiment of the invention, Form 12 can be characterized by the differential scanning calorimetry profile (DSC) shown in FIG. 15. The DSC graph plots the heat flow as a function of temperature from a sample, the temperature rate change being about 10° C./min. The profile is characterized by two endothermic transitions. The first is has an onset temperature of about 38.8° C., with a melt at about 71.3° C. (peak maximum). The second endothermic transition is a weak transition with an onset temperature of about 201.3° C. These temperatures have an error of ±2° C.

Figure 16:
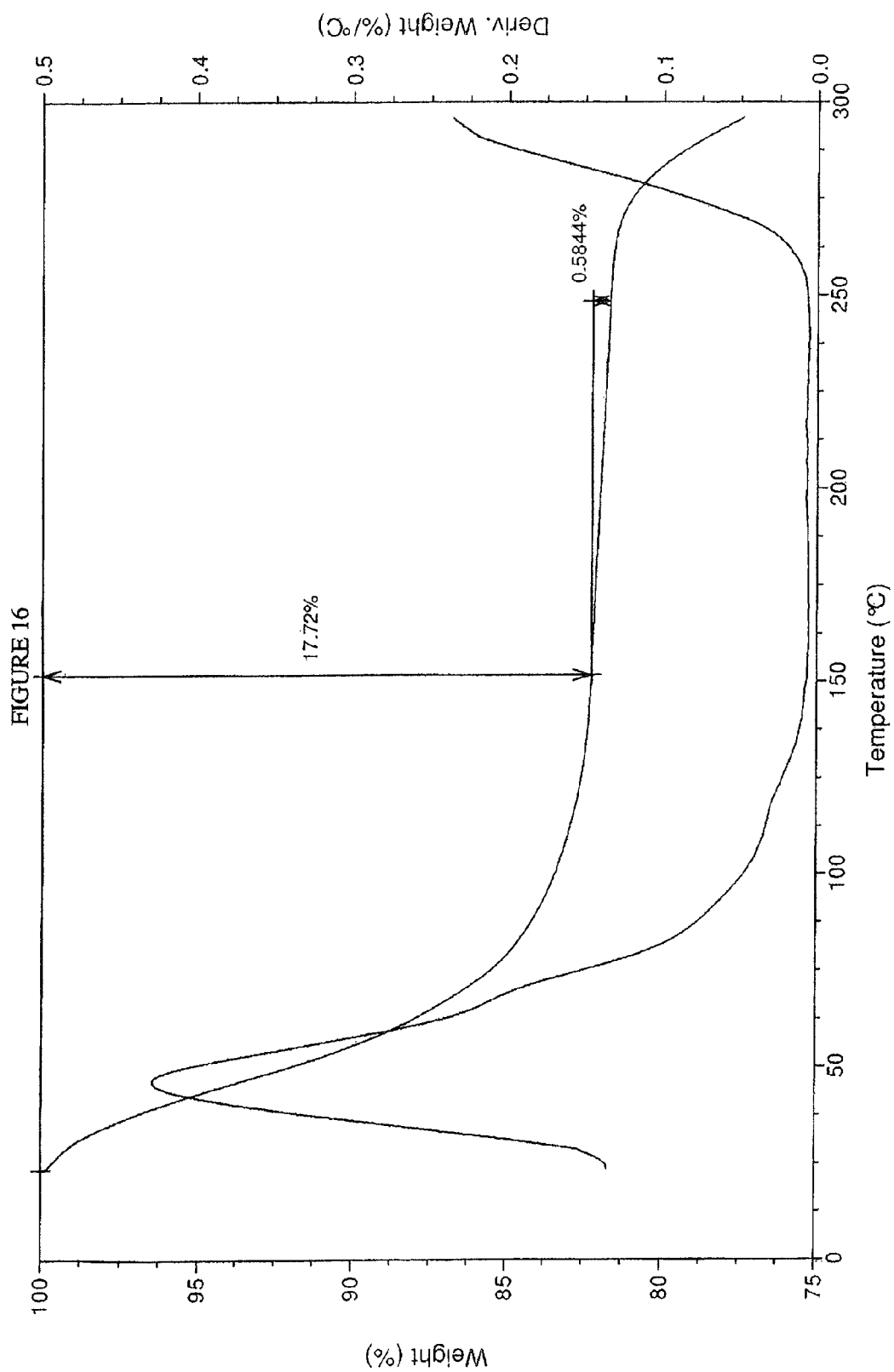
FIG. 16 is a thermal gravimetric analysis (TGA) profile for sodium 4-{[9-chloro-7-(2-fluoro-6-methoxyphenyl)-5H-pyrimido[5,4-d][2]benzazepin-2-yl]amino}-2-methoxybenzoate Form 12.

In another embodiment of the invention, Form 12 can be characterized by the thermal gravimetric analysis (TGA) shown in FIG. 16, which graphs the percent loss of weight of the sample as a function of temperature, the temperature rate change being about 10° C./min. The weight loss represents a loss of about 18.3% of the weight of the sample as the temperature is changed from 25° C. to 250° C.

In another embodiment of the invention, Form 12 is characterized by at least one of the following features (VI-i)-(VI-iv):

(VI-i) at least one of the X-ray powder diffraction peaks shown in Table 6;
(VI-ii) an X-ray powder diffraction pattern substantially similar to FIG. 14;
(VI-iii) a differential scanning calorimetry (DSC) profile substantially similar to FIG. 15; and
(VI-iv) a thermal gravimetric analysis (TGA) substantially similar to FIG. 16.

In a further embodiment of the invention, a single crystalline form of Form 12 is characterized by two of the features (VI-i)-(VI-iv). In a further embodiment of the invention, a single crystalline form of Form 12 is characterized by three of the features (VI-i)-(VI-iv). In a further embodiment of the invention, a single crystalline form of Form 12 is characterized by all of the features (IV-i)-(IV-iii).

Form 24

Figure 17:
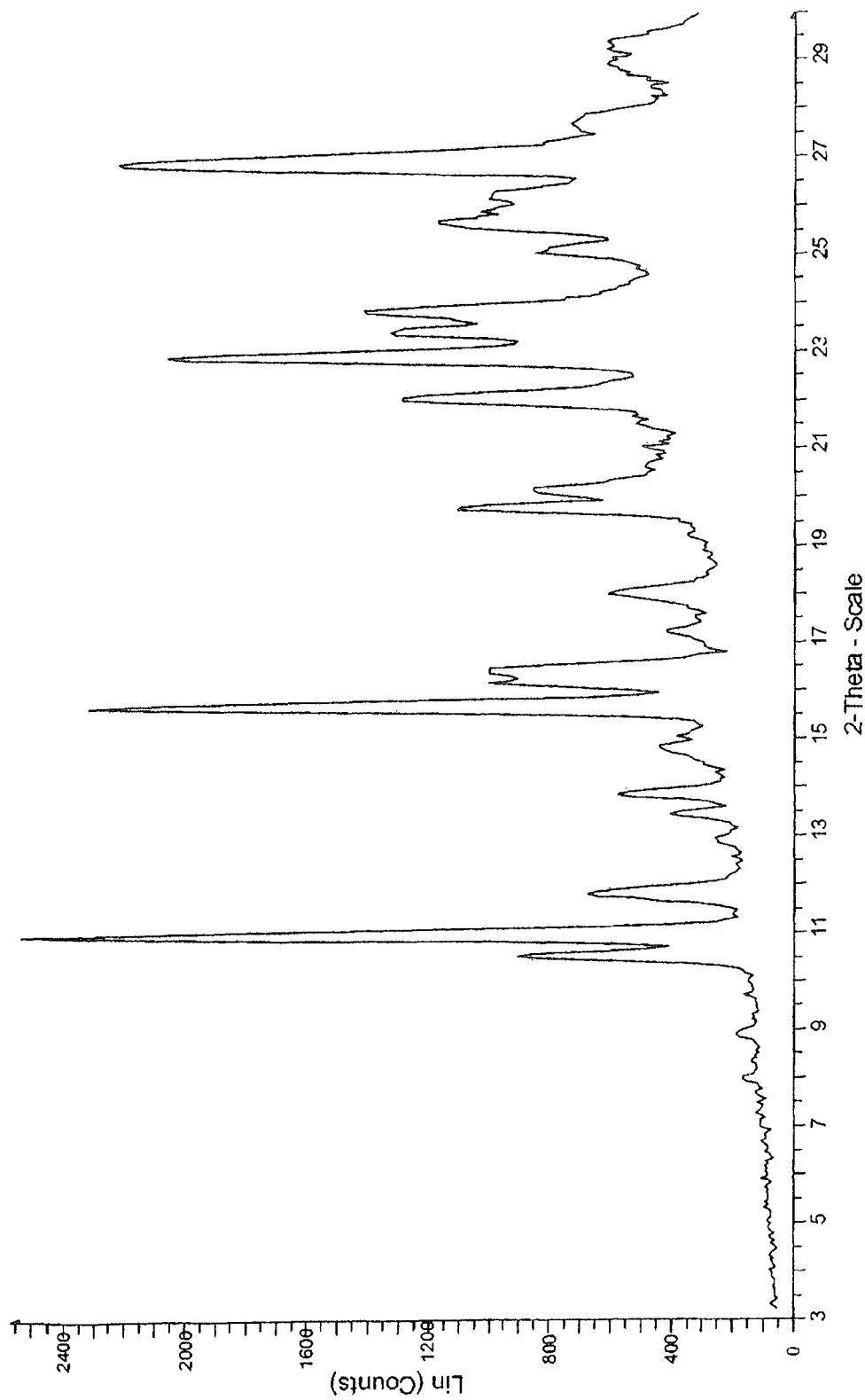
FIG. 17 is a powder X-ray diffractogram (XRPD) of sodium 4-{[9-chloro-7-(2-fluoro-6-methoxyphenyl)-5H-pyrimido[5,4-d][2]benzazepin-2-yl]amino}-2-methoxybenzoate Form 24.

In one embodiment of the invention, a single crystalline form, Form 24, of the Sodium Salt is characterized by the X-ray powder diffraction (XRPD) pattern shown in FIG. 17, and data shown in Table 7, obtained using CuKα radiation. In a particular embodiment of the invention, the polymorph can be characterized by one or more of the peaks taken from FIG. 17.

TABLE 7

| Angle 2-Theta ° | Intensity % |
|---|---|
| 7.96 | 6.4 |
| 8.86 | 7.3 |
| 10.49 | 36.2 |
| 10.93 | 100 |
| 11.81 | 26.5 |
| 12.90 | 10.7 |
| 13.46 | 16.1 |
| 13.85 | 22.7 |

TABLE 7-continued

| Angle 2-Theta ° | Intensity % |
|---|---|
| 14.82 | 17.1 |
| 15.67 | 91.3 |
| 16.17 | 39.8 |
| 16.39 | 40.2 |
| 17.22 | 16.3 |
| 18.01 | 24.0 |
| 19.76 | 44.2 |
| 20.16 | 34.4 |
| 22.05 | 50.6 |
| 22.90 | 81.1 |
| 23.38 | 52.7 |
| 23.84 | 56.2 |
| 25.05 | 33.2 |
| 25.70 | 46.0 |
| 26.18 | 39.7 |
| 26.91 | 87.4 |

In another embodiment of the invention, the peaks are identified at 2θ angles of 10.93°, 15.67°, 19.76°, 22.05°, 22.90°, 23.38°, 23.84°, and 26.91°. In a further particular embodiment, the peaks are identified at 2θ angles of 10.93°, 15.67°, 22.90°, 23.84°, and 26.91°.

Figure 18:
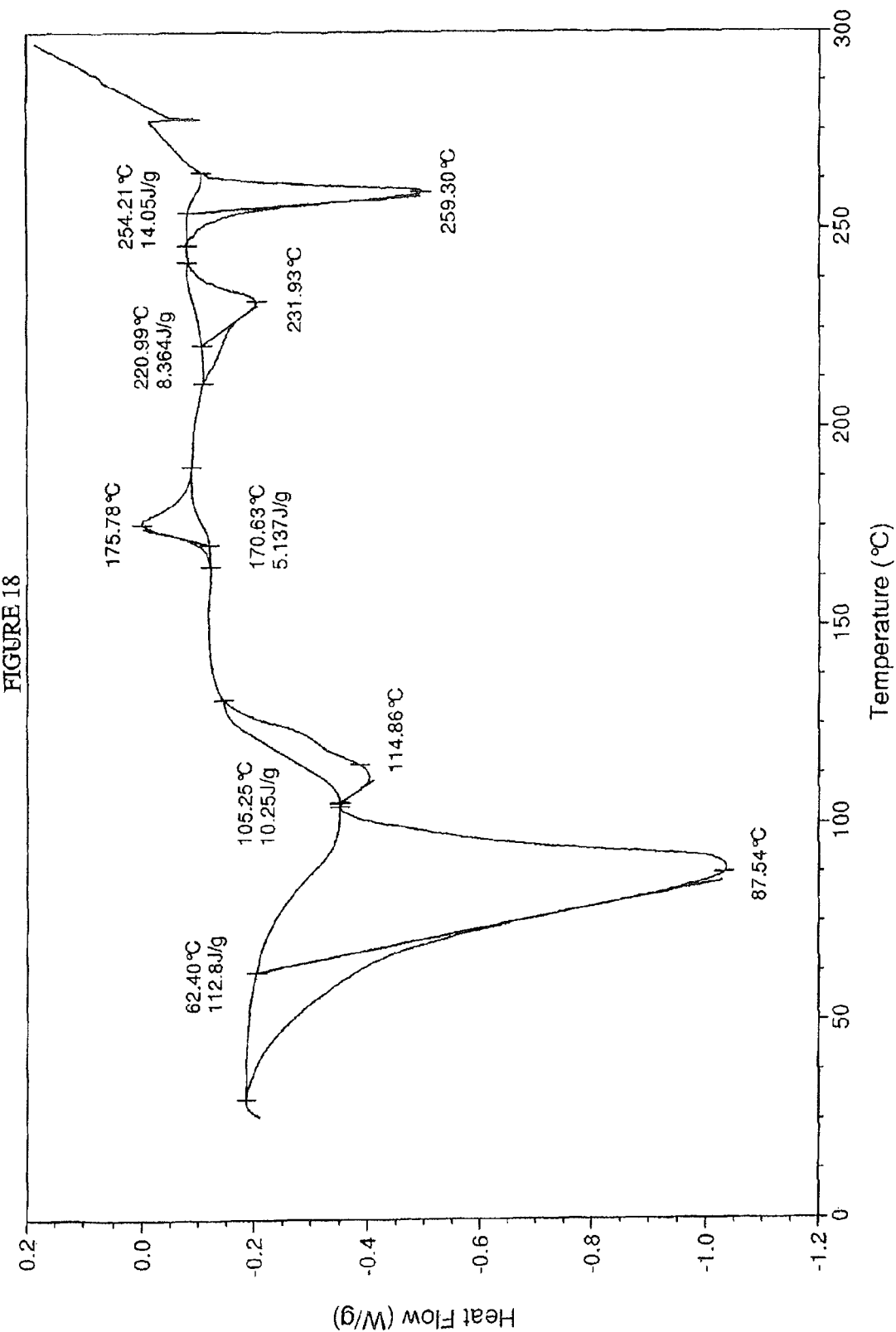
FIG. 18 is a differential scanning calorimetry (DSC) profile for sodium 4-{[9-chloro-7-(2-fluoro-6-methoxyphenyl)-5H-pyrimido[5,4-d][2]benzazepin-2-yl]amino}-2-methoxybenzoate Form 24.

In another embodiment of the invention, Form 24 can be characterized by the differential scanning calorimetry profile (DSC) shown in FIG. 18. The DSC graph plots the heat flow as a function of temperature from a sample, the temperature rate change being about 10° C./min. The profile is characterized by several exothermic and endothermic transitions. The first is an endothermic transition with an onset temperature of about 62.4° C., with a melt at about 87.5° C. (peak maximum), followed by a weak endothermic transition with an onset temperature of about 105.3° C. The next is an exothermic transition at about 175.8° C., followed by an endothermic transition has an onset temperature of about 221.0° C., with a melt at about 231.9° C. (peak maximum). The final transition is endothermic and has an onset temperature of about 254.2° C., with a melt at about 259.3° C. (peak maximum). These temperatures have an error of ±2° C.

Figure 19:
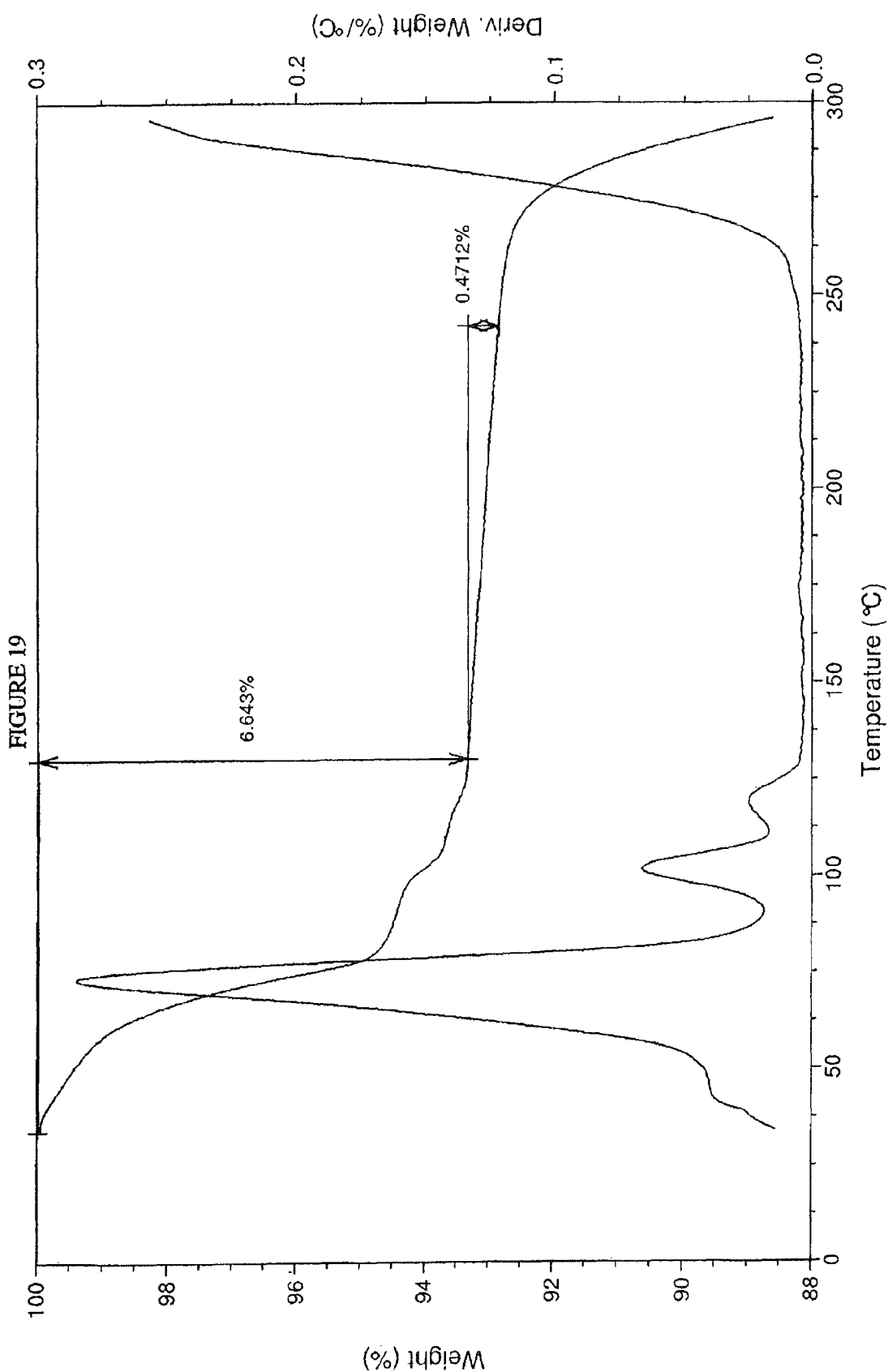
FIG. 19 is a thermal gravimetric analysis (TGA) profile for sodium 4-{[9-chloro-7-(2-fluoro-6-methoxyphenyl)-5H-pyrimido[5,4-d][2]benzazepin-2-yl]amino}-2-methoxybenzoate Form 24.

In another embodiment of the invention, Form 24 can be characterized by the thermal gravimetric analysis (TGA) shown in FIG. 19. The TGA profile graphs the percent loss of weight of the sample as a function of temperature, the temperature rate change being about 10° C./min. The weight loss represents a loss of about 7.1% of the weight of the sample as the temperature is changed from 25° C. to 250° C.

In another embodiment of the invention, Form 24 is characterized by at least one of the following features (VII-i)-(VII-iv):

(VII-i) at least one of the X-ray powder diffraction peaks shown in Table 7;
(VII-ii) an X-ray powder diffraction pattern substantially similar to FIG. 17;
(VII-iii) a differential scanning calorimetry (DSC) profile substantially similar to FIG. 18; and
(VII-iv) a thermal gravimetric analysis (TGA) profile substantially similar to FIG. 19.

In a further embodiment of the invention, a single crystalline form of Form 24 is characterized by two of the features (VII-i)-(VII-iv). In a further embodiment of the invention, a single crystalline form of Form 24 is characterized by three of the features (VII-i)-(VII-iv). In a further embodiment of the invention, a single crystalline form of Form 24 is characterized by all of the features (IV-i)-(IV-iv).

Other embodiments of the invention are directed to a single crystalline form of the Sodium Salt characterized by a combination of the aforementioned characteristics of any of the single crystalline forms discussed herein. The characterization may be by any combination of one or more of the XRPD, TGA, DSC, and water sorption/desorption measurements described for a particular polymorph. For example, the single crystalline form of the Sodium Salt may be characterized by any combination of the XRPD results regarding the position of the major peaks in a XRPD scan; and/or any combination of one or more of the cell parameters derived from data obtained from a XRPD scan. The single crystalline form of the Sodium Salt may also be characterized by TGA determinations of the weight loss associated with a sample over a designated temperature range; and/or the temperature at which a particular weight loss transition begins. DSC determinations of the temperature associated with the maximum heat flow during a heat flow transition and/or the temperature at which a sample begins to undergo a heat flow transition may also characterize the crystalline form. Weight change in a sample and/or change in sorption/desorption of water per molecule of anhydrous Sodium Salt as determined by water sorption/desorption measurements over a range of relative humidity (e.g., 0% to 90%) may also characterize a single crystalline form of the Sodium Salt.

Examples of combinations of single crystalline form characterizations using multiple analytical techniques include the location of at least one of the major peaks of a XRPD scan and the temperature associated with the maximum heat flow during one or more heat flow transitions observed by a corresponding DSC measurement; the location of at least one of the major peaks of a XRPD scan and one or more weight losses associated with a sample over a designated temperature range in a corresponding TGA measurement; the location of at least one of the major peaks of a XRPD scan, the temperature associated with the maximum heat flow during one or more heat flow transitions observed by a corresponding DSC measurement, and one or more weight losses associated with a sample over a designated temperature range in a corresponding TGA measurement; and the location of at least one of the major peaks of a XRPD scan, the temperature associated with the maximum heat flow during one or more heat flow transitions observed by a corresponding DSC measurement, one or more weight losses associated with a sample over a designated temperature range in a corresponding TGA measurement, and the change in sorption/desorption of water per molecule of anhydrous salt as determined by water sorption/desorption measurements over a range of relative humidity. As well, each of the aforementioned examples may replace the use of the location of at least one of the major peaks of a XRPD scan with one or more cell parameters of the single crystalline form.

The combinations of characterizations that are discussed above may be used to describe any of the polymorphs of the Sodium Salt discussed herein (e.g., Form 1, 2, 4, 6, 11, 12, or 24).

In some embodiments, Form 6 can be converted to give Form 2. In some other embodiments, Form 6 can be converted to give Form 2 by heating at a temperature of between about 25° C. and about 50° C. In yet some other embodiments, Form 6 can be converted to give a mixture of Form 6 and Form 2.

In some embodiments, Form 11 can be converted to give Form 1, Form 2, or a mixture therof. In some other embodiments, Form 11 can be converted to give Form 1, Form 2, or a mixture thereof by heating at a temperature of between about 25° C. and about 50° C. In yet some other embodiments, Form 11 can be converted to give a mixture of any combination of Form 1, Form 2, Form 11, and Form 24.

In some embodiments, Form 1 can be converted to give Form 24. In some other embodiments, Form 1 can be converted to give Form 24 by standing at ambient conditions. In yet some other embodiments, Form 1 can be converted to give a mixture of any combination of Form 1, Form 2, and Form 24.

In some embodiments, Form 4 can be converted to give Form 24. In some other embodiments, Form 4 can be desolvated to give Form 24 by drying under ambient conditions. In yet some other embodiments, Form 4 can be converted to give a mixture of any combination of Form 1, Form 2, Form 4 and Form 24.

In some embodiments, Form 24 can be converted to give Form 1, Form 2, or a mixture thereof. In some other embodiments, Form 24 can be converted to give Form 1 by heating at a temperature of between about 50° C. and about 75° C. In some other embodiments, Form 24 can be converted to give Form 2 by heating at a temperature of between about 25° C. and about 50° C. In yet some other embodiments, Form 24 can be converted to give a mixture of any combination of Form 1, Form 2, and Form 24.

Pharmaceutical Compositions and Methods

The pharmacological properties of the Sodium Salt, or crystalline forms thereof, is such that it is suitable for use in the treatment of patients suffering from or subject to diseases, disorders or conditions mediated by Aurora kinase, including, but not limited to, proliferative disorders such as chronic inflammatory proliferative disorders, e.g., psoriasis and rheumatoid arthritis; proliferative ocular disorders, e.g., diabetic retinopathy; benign proliferative disorders, e.g., hemangiomas; and cancer.

In certain embodiments of the invention, a method for treating cancer is provided comprising administering a pharmaceutically effective amount of the Sodium Salt, or a crystalline form thereof, or a pharmaceutical composition thereof, to a subject in need thereof.

In some embodiments, the cancer is a solid tumor. Non-limiting examples of solid tumors that can be treated by the methods of the invention include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors e.g., neuroblastoma; brain tumors, including, e.g., glioma, anaplastic oligodendroglioma, adult glioblastoma multiforme, and adult anaplastic astrocytoma; bone cancer; and soft tissue sarcoma.

In some other embodiments, the cancer is a hematologic malignancy. Non-limiting examples of hematologic malignancy include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideblasts (RARS), refractory anemia with excess blasts (RAEB), and RAEB in transformation (RAEB-T); and myeloproliferative syndromes.

In still other embodiments, the cancer is selected from the group consisting of NHL, AML, MDS, colorectal cancer, ovarian cancer, breast cancer, gastric cancer, prostate cancer, and pancreatic cancer.

Some embodiments of the invention are directed toward a solid pharmaceutical composition comprising at least one pharmaceutically acceptable carrier or diluent; and the Sodium Salt, or a crystalline form thereof. In other embodiments, the solid pharmaceutical composition comprises at least one pharmaceutically acceptable carrier or diluent, and a substantially crystalline Sodium Salt. In other embodiments, the solid pharmaceutical composition comprises at least one pharmaceutically acceptable carrier or diluent, and the Sodium Salt, wherein the Sodium Salt is at least 95% by weight a single crystalline form; the single crystalline forms being described herein. In other embodiments, the solid pharmaceutical composition comprises at least one pharmaceutically acceptable carrier or diluent, and the Sodium Salt, wherein the Sodium Salt is substantially a single crystalline form; the single crystalline forms being described herein. In other embodiments, these solid compositions optionally further comprise one or more additional therapeutic agents.

Some embodiments of the invention are directed toward a liquid pharmaceutical composition comprising at least one pharmaceutically acceptable carrier or diluent; and the compound 4-{[9-chloro-7-(2-fluoro-6-methoxyphenyl)-5H-pyrimido[5,4-d][2]benzazepin-2-yl]amino}-2-methoxybenzoic acid of formula (II). In some embodiments, the liquid pharmaceutical composition is prepared using a substantially crystalline Sodium Salt. In other embodiments, the liquid pharmaceutical composition is prepared using the Sodium Salt, wherein the Sodium Salt is at least 95% by weight a single crystalline form; the single crystalline forms being described herein. In other embodiments, the liquid pharmaceutical is prepared using the Sodium Salt, wherein the Sodium Salt is substantially a single crystalline form; the single crystalline forms being described herein. In other embodiments, these liquid compositions optionally further comprise one or more additional therapeutic agents.

As described above, the pharmaceutically acceptable compositions of the present invention additionally comprise at least one pharmaceutically acceptable carrier, which, as used herein, includes any and all solvents, diluents, or other liquid vehicle, dispersion or suspension aids, gelatin or polymeric capsule shell, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, sodium bicarbonate, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The Sodium Salt, or a single crystalline form thereof, or a pharmaceutical composition thereof, according to the method of the present invention, may be administered using any amount and any route of administration effective for treating the disease. The exact amount required will vary from subject to subject, depending on the species, age, and general condition of the subject, the severity of the infection, the particular agent, its mode of administration, and the like. The Sodium Salt, or a single crystalline form thereof, or a pharmaceutical composition thereof, are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disease being treated and the severity of the disease; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The Sodium Salt, or a single crystalline form thereof, or a pharmaceutical composition thereof, can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound. Alternatively, compositions for rectal or vaginal administration are gels or creams that can be prepared by mixing compounds with suitable non-irritating excipients such as oils or water to solubilize the compound and polymers and fatty alcohols can be added to thicken the formulation to increase the residual time in the rectal or vaginal cavity and release the active compound.

Solid dosage forms for oral administration include capsules, tablets, pills, powders, and granules. In such solid dosage forms, the active compound may optionally be mixed with at least one inert, pharmaceutically acceptable excipient or carrier such as sodium citrate or dicalcium phosphate and/ or a) fillers or extenders such as starches, lactose, sucrose, glucose, mannitol, microcrystalline cellulose, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, croscarmellose sodium, potato or tapioca starch, alginic acid, certain silicates, crospovidone, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, sodium stearyl fumarate, and mixtures thereof. In the case of capsules, tablets and pills, the dosage form may also comprise buffering agents or a flow aid such as colloidal silicon dioxide. In other embodiments, the active compound may be encapsulated in a gelatin or polymeric capsule shell without any additional agents (neat capsule shell).

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. The solid dosage forms may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

In some embodiments, the solid dosage form comprises the Sodium Salt, or a crystalline form thereof, and at least one of sodium stearyl fumarate, crospovidone, mannitol and colloidal silicon dioxide.

In some embodiments, the solid dosage form comprises a tablet with a film coating. In some other embodiments, the solid dosage form comprises about 10% of a lubricant. In some other embodiments, the solid dosage form comprises about 9% of a disintegrant. In some embodiments, the solid dosage form has a high drug loading. In some embodiments, the solid dosage form comprises about 30% to about 60% by weight of the Sodium Salt, or a crystalline form thereof. In some embodiments, the solid dosage form comprises about 40% to about 50% by weght of the Sodium Salt, or a crystalline form thereof.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The Sodium Salt, or a single crystalline form thereof, or pharmaceutical composition thereof, may be used in an application of monotherapy to treat a disorder, disease or symptom, it also may be used in combination therapy, in which the use of an inventive compound or composition (therapeutic agent) is combined with the use of one or more other therapeutic agents for treating the same and/or other types of disorders, symptoms and diseases. Combination therapy includes administration of the therapeutic agents concurrently or sequentially. Alternatively, the therapeutic agents can be combined into one composition which is administered to the patient.

Another aspect of the invention describes a process for the synthesis of the compound of Formula (II) as outlined herein.

EXAMPLES

Abbreviations

| Abbreviations | |
|---|---|
| ca | approximately |
| DMSO | dimethylsulfoxide |
| DSC | differential scanning calorimetry |
| EtOH | ethanol |
| GC | gas chromatography |
| GVS | gravimetric vapor sorption |
| h | hours |
| HPLC | high performance liquid chromatography |
| KF | Karl Fischer |
| min | minutes |
| m/z | mass to charge |
| MS | mass spectrum |
| MTBE | tent-butyl methyl ether |
| NMR | nuclear magnetic resonance |
| RT | room temperature |
| TGA | thermal gravimetric analysis |
| XRPD | X-ray powder diffraction |

General Methods $^1$H NMR: Proton nuclear magnetic resonance spectra are obtained on either:
  i) a Brucker 400 MHz spectrometer equipped with an autosampler (samples are prepared in $d_6$-DMSO, unless otherwise stated); or
  ii) a Varian Mercury 300 MHz spectrometer.

Mass Spectrometry: Mass spectrometry studies are run on a Thermo-Finnigan LCQ Deca-XP ion trap mass spectrometer. The electrospray ion source was used in both positive and negative modes with a high voltage of 5 kv, sheath gas flow rate of 35 arb, capillary temperature of 275° C., capillary voltage of 9 V and tube lens offset of 35 V. An analyte was dissolved in acetonitrile to generate a 0.5 mg/ml solution. An Agilent 1100 HPLC system was used for LC-Mass spectrometry flow analysis. The pump flow rate was 1.0 ml/minute. 10 µl of each sample solution was injected from the autosampler into a T-joint. About 2% of the solution from the T-joint was infused into the mass spectrometer.

X-Ray Powder Diffractometry (XRPD): X-ray powder diffraction patterns are acquired on either:
  i) a Bruker AXS/Siemens D5000 diffractometer using Cu Kα radiation (40 kV, 40 mA), θ-θ goniometer, automatic divergence and receiving slits, a graphite secondary monochromator and a scintillation counter. The instrument is performance checked using a certified corundum standard (NIST 1976). Samples run under ambient conditions are prepared as flat plate specimens using powder as received without grinding. Approximately 35 mg of the sample is gently packed into a cavity cut into polished, zero-background (510) silicon wafer. The sample is rotated in its own plane during analysis. Samples run under non-ambient conditions are packed into a stainless steel cavity sample holder equipped with a Pt 100 thermocouple. Low temperature data are collected using an Anton Paar TTK450 variable temperature camera attached to the Bruker AXS/Siemens D5000 diffractometer. Instrumental conditions for the low temperature scan are similar to those described for the flat plate samples above. All XRPD analyses are performed using the Diffrac Plus XRD Commander software v2.3.1. Diffraction data are reported using Cu Kα1 (λ=1.5406 Å), after the Kα2 component has been stripped using EVA, the powder patterns are indexed by the ITO method using WININDEX and the raw lattice constants refined using WIN-METRIC; or
  ii) a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. The beam divergence, i.e. the effective size of the X-ray beam on the sample, is approximately 5 mm. A θ-θ continuous scan mode is employed with a sample, detector distance of 20 cm which gives an effective 2θ range of 3.2°-29.7°. Typically, the sample would be exposed to the X-ray beam for 120 seconds. Samples run under ambient conditions are prepared as flat plate specimens using powder without grinding. Approximately 1-2 mg of the sample is lightly pressed on a glass slide to obtain a flat surface. Samples run under non-ambient conditions are mounted on a silicon wafer with heatconducting compound. The sample is then heated to the appropriate temperature at ca. 20° C. per min and subsequently held isothermally for ca 1 minute before data collection is initiated; or
  iii) a Brucker AZS D8-Advance X-ray Diffractometer. About 50 mg of sample is gently flattened into a 50 mm diameter quartz sampling pan for powder measurements. The sample is run as a continuous scan from 2.9°2θ to 29.6°2θ using 2θ/θ locked coupled angles. Each angle interval is 0.05°2θ and the data are collected for 2 seconds. The sample run occurs under ambient conditions and data analysis is performed using EVA version 9.0 software.

Differential Scanning calorimetry (DSC): Differential scanning calorimetry (DSC) data are collected on either:

i) a TA Instruments Q1000 differential scanning calorimeter equipped with a 50 position auto-sampler. The energy and temperature calibration standard is indium. Samples are heated at a rate of 10° C. per minute between 25° C. and 300° C. A nitrogen purge flowing at 30 mL per minute is maintained over the sample during a scan. Between 0.5 mg and 3 mg of sample is analyzed. All samples are crimped in a hermetically sealed aluminum pan with a pinhole to alleviate the pressure accumulated from the solvent vapor; or ii) a TA Instruments DSC Q2000 differential scanning calorimeter. Between 1 mg and 2 mg of sample is sealed in an aluminum pan with a lid. The sample is heated at a ramp rate of 10° C. per minute between 25° C. and 350° C., while the nitrogen sample puge is kept constant at 50 mL/min. The thermograms are analyzed using Thermal Advantage for Q Series software.

Thermal Gravimetric Analysis (TGA): Thermal gravimetric analysis (TGA) data are collected on a TA Instruments Q500 thermal gravimetric analyzer, equipped with a 16 position auto-sampler. The instrument is calibrated using certified Alumel. Typically 3 mg to 10 mg of sample is loaded onto a pre-tared platinum crucible and aluminum DSC pan, heated at 10° C. per minute from ambient temperature to 350° C. A nitrogen purge flowing at 60 mL per minute is maintained over the sample during measurements. The thermograms are analyzed using Thermal Advantage for Q Series software.

Example 1

Synthesis of (5-chloro-2-iodophenyl)(2-fluoro-6-methoxyphenyl)methanone (3)

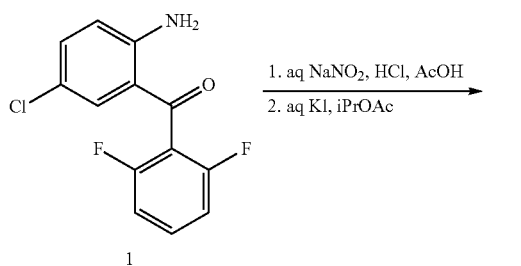

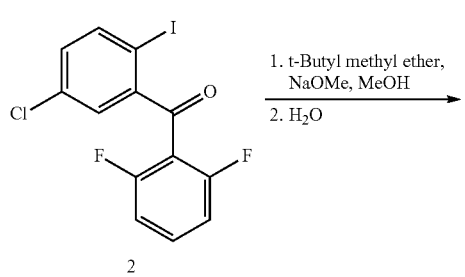

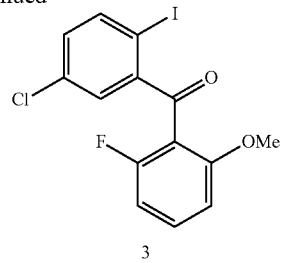

Step 1: (5-chloro-2-iodophenyl)(2,6-difluorophenyl)methanone (2)

Into a reactor at room temperature was added (2-amino-5-chlorophenyl)(2,6-difluorophenyl)methanone (1, 60.0 kg, 224 mol) and acetic acid (427 L). The mixture was stirred until all solids fully dissolved, filtered and washed with acetic acid (9.47 L). Concentrated HCl (156 L) was added over a minimum of 30 minutes at 20 to 25° C. and the resulting mixture was cooled to 0 to 5° C. A solution of sodium nitrite (18.6 kg, 269 mol) in water (88.0 L) was added while maintaining the reaction temperature between 0 and 5° C. The mixture was stirred for 1 h at 0 to 5° C. Water (270 L) and isopropyl acetate (717 L) were then added at 0 to 5° C. A solution of potassium iodide (50.2 kg, 303 mol) in water (133 L) was added over 1 h at 0 to 5° C. The reaction mixture was stirred for 30 min and warmed to 20 to 25° C. over 1.5 h. The layers were separated and the organic phase was washed with a dilute brine solution (22 kg NaCl in 200 L water) and a sodium carbonate solution (175 kg $Na_2CO_3$ in 523 L water). The resulting organic layer was washed twice with a sodium ascorbate solution (15.8 kg in 188 L water for each wash) followed by water (200 L). The organic phase was concentrated using a maximum 50° C. jacket temperature until 430 L of solvent was removed. Heptane (400 L) was added and the mixture was concentrated using a 50° C. jacket temperature until 395 L of solvent were removed. 2-Butanol (398 L) was added and the mixture was concentrated using a maximum 60° C. jacket temperature until 322 L of solvent were removed. An additional portion of 2-butanol (398 L) was added and the mixture was concentrated using a 70° C. jacket temperature until 390 L of solvent were removed. The reaction mixture was cooled to −5 to −8° C., stirred for 2 h, filtered and washed with 2-butanol (2×84.2 L) at −5 to 0° C. The resulting wet cake was dried at 40 to 50° C. under vacuum to provide 67.6 kg (80% yield) of 2. $^1$H NMR (300 MHz, $CDCl_3$) δ 7.89 (d, J=8.2 Hz, 1H), 7.51 (m, 1H), 7.44 (d, J=2.3 Hz, 1H), 7.18 (dd, J=2.3, 8.2 Hz, 1H), 7.00 (m, 2H); Elemental Anal. Calcd. for $C_{13}H_6ClF_2IO$: C, 41.25; H, 1.60; Cl, 9.37; F, 10.04; I, 33.52; O, 4.23. Found: C, 41.36; H, 1.65; Cl, 9.51; F, 10.03; I, 33.41; O, 4.04.

Step 2: (5-chloro-2-iodophenyl)(2-fluoro-6-methoxyphenyl)methanone (3)

Into a reactor at room temperature was added 2 (67.6 kg, 179 mol) and MTBE (344 L). The mixture was warmed to 40° C. and stirred for 30 min until solids fully dissolved. The mixture was then cooled to 25 to 30° C. Sodium methoxide as a 25% w/w solution in methanol (45.2 kg, 209 mol) was added over a minimum of 90 min at 25 to 30° C. The reaction mixture was stirred for at least 2 h until >99.0% conversion was obtained by HPLC analysis. Water (483 L) was added slowly over 30 min while maintaining the temperature between 20 and 25° C. The layers were separated and the aqueous phase was extracted with MTBE (77 L). The combined organic extracts were washed with a dilute brine solution (38 kg NaCl in 342 L water). The organic layer was filtered, washed with water (242 L) and the organic phase was filtered. The resulting organic phase was concentrated until 360 L of solvent were removed while maintaining the internal temperature below 70° C. Isobutanol (302 L) was added and the mixture was concentrated while maintaining the internal temperature below 70° C. until 307 L of solvent were removed. A second portion of isobutanol (330 L) was added and the mixture was concentrated while maintaining the internal temperature below 70° C. until 210 L of solvent were removed. The mixture was heated to 60 to 85° C. until a clear solution was obtained and cooled to 50° C. A slurry of seed crystals (50 g in 150 mL isobutanol) was added and the mixture was cooled to 40° C. A second slurry of seed crystals (30 g in 60 mL isobutanol) was added and the mixture was cooled to 20 to 25° C. over a minimum of 3 h. The resulting mixture was stirred an additional 2 h. The mixture was filtered and washed with isobutanol (2×65 L). The resulting wet cake was dried at 20 to 35° C. under vacuum to provide 50.9 kg of crude 3. Into a separate reactor was charged crude 3 and isobutanol (69 L). The mixture was heated to 75 to 80° C. until a clear solution was obtained. The reaction mixture was cooled to 55° C. and a slurry of seed crystals (50 g in 500 mL isobutanol) was added. The mixture was stirred for 30 min at 55° C., cooled to 20 to 25° C. over a minimum of 3 h and stirred an additional 2 h. The mixture was filtered and washed with isobutanol (2×31 L). The wet cake was dried under vacuum at 40° C. to provide 46.0 kg (66% yield) of purified 3. $^1$H NMR (300 MHz, CDCl$_3$) δ 7.88 (d, J=8.2 Hz, 1H), 7.42 (m, 2H), 7.13 (dd, J=2.3, 8.2 Hz), 6.76 (m, 2H), 3.73 (s, 3H); MS (ESI) m/z 391.2 (M+H$^+$, 30%).

Example 2

Synthesis of 4-{[amino(imino)methyl]amino}-2-methoxybenzoic acid hydrochloride (6)

Step 1: methyl 4-{[amino(imino)methyl]amino}-2-methoxybenzoate nitrate (5)

Into a reactor at room temperature was added methyl 4-amino-2-methoxybenzoate (4, 38 kg, 210 mol) and methanol (224 L). The mixture was stirred at 25 to 30° C. for 30 min. Aqueous cyanamide (50% w/w, 43 kg, 512 mol) was added over a minimum of 30 min at 20 to 25° C. The reaction mixture was heated to reflux using a maximum jacket temperature of 75° C. Concentrated nitric acid (45 kg, 499 mol) was added over a minimum of 60 min. The resulting mixture was heated at reflux for 2 h. A suspension of seed crystals (16 g in 600 mL methanol) was added and the mixture was stirred using a 75° C. jacket temperature for 60 to 90 min. The mixture was cooled to 20 to 25° C. over at least 2 h and stirred for an additional 2 h. The mixture was filtered and washed with methanol (180 L) while stirring for 1 h. The wet cake was washed a second time with methanol (180 L) while stirring for 1 h. The resulting wet cake was dried under vacuum at 25° C. to provide 30.0 kg (50% yield) of 5. $^1$H NMR (300 MHz, DMSO-d$_6$) δ 9.82 (s, 1H), 7.70 (d, J=8.2 Hz, 1H), 7.57 (s, 4H), 6.97 (d, J=2.3 Hz, 1H), 6.84 (dd, J=2.3, 8.2 Hz, 1H), 3.81 (s, 3H), 3.76 (s, 3H); MS (ESI) m/z 224.4 (M$^+$, 100%).

Step 2: 4-{[amino(imino)methyl]amino}-2-methoxybenzoic acid hydrochloride (6)

Into a reactor was added 5 (29.8 kg, 104 mol) and water (475 L). The mixture was heated to 75 to 80° C. and concentrated HCl (107 kg, 1051 mol) was added over a minimum of 30 min while maintaining the temperature between 75 and 80° C. The reaction mixture was stirred for 3 h at 75 to 80° C. The reaction mixture was sampled and the % conversion was determined by HPLC analysis. The mixture was heated at 75 to 80° C. until the % conversion reached >97.3% or until at total reaction time of 7 h. The reaction was cooled to 20 to 25° C. over a minimum of 3 h and stirred for an additional 2 h at 20 to 25° C. The reaction was filtered and washed with 16% w/w HCl (2×35 kg), water (82 L) and heptane (2×120 L). The resulting wet cake was dried under vacuum at 35 to 50° C. to provide 23.9 kg (93% yield) of 6. $^1$H NMR (300 MHz, DMSO-d$_6$) δ 10.25 (s, 1H), 7.72 (s, 4H), 7.69 (d, J=8.8 Hz, 1H), 6.93 (d, J=2.3 Hz, 1H), 6.81 (dd, J=2.3, 8.8 Hz, 1H), 3.80 (s, 3H); MS (ESI) m/z 210.4 (M$^+$, 100%).

Example 3

Synthesis of sodium 4-{[9-chloro-7-(2-fluoro-6-methoxyphenyl)-5H-pyrimido[5,4-d][2]benzazepin-2-yl]amino}-2-methoxybenzoate polymorph Form 1 and Form 2.

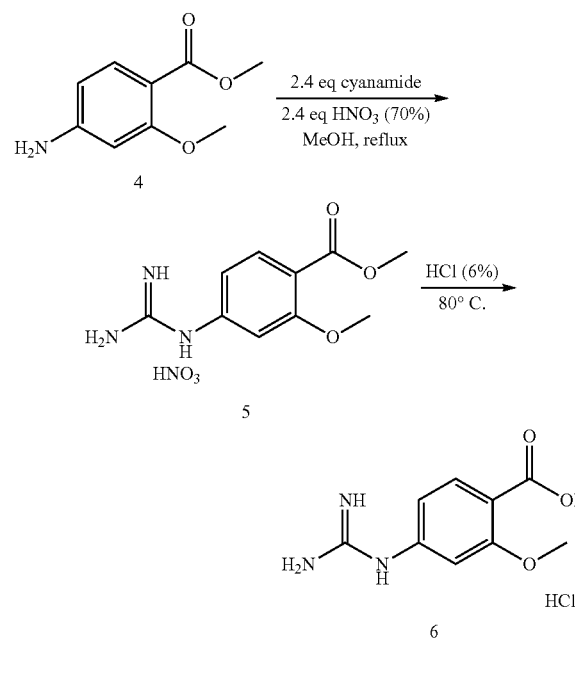

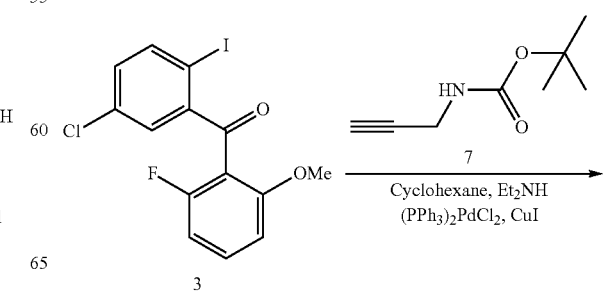

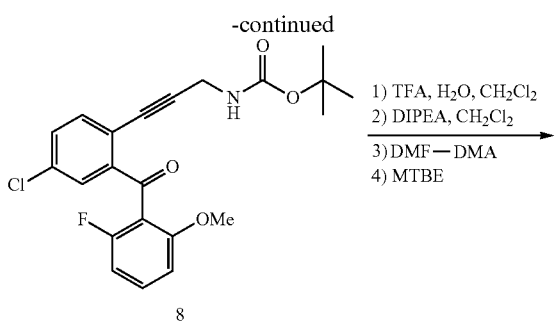

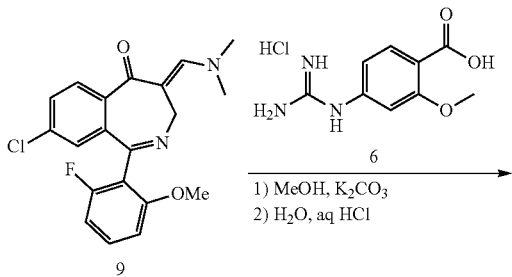

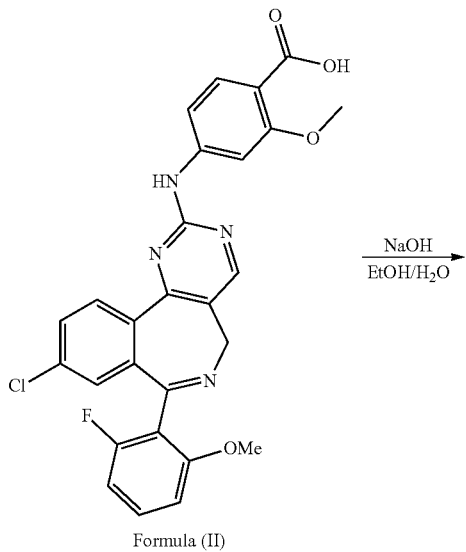

Formula (II)

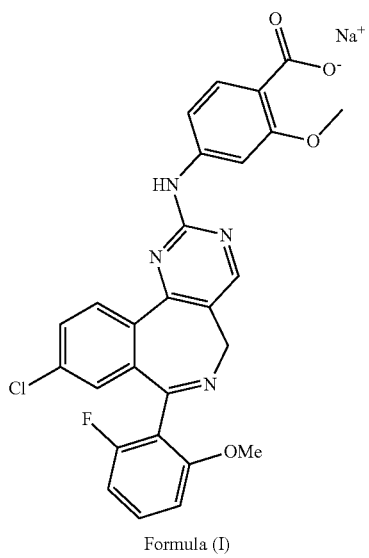 [SMILES: COc1cc(Nc2ncc3c(n2)-c2ccc(Cl)cc2C(c2c(F)cccc2OC)=NC3)ccc1C(=O)[O-] ; [Na+]]

Formula (I)

Step 1: tert-butyl prop-2-yn-1-ylcarbamate (7)

Into a reactor was added propagylamine (10.0 kg, 182 mol) and MTBE (154 L). A Boc$_2$O solution was prepared by dissolving Boc$_2$O (41.3 kg, 190 mol) in MTBE (61 L) and transferred over a minimum of 60 min to the propargyamine solution while maintaining a temperature between 23 and 28° C. The reaction mixture was stirred for at least 1 h until ≥98.0% conversion was obtained by GC analysis. A solution of sodium bisulfate (5.6 kg of NaHSO$_4$ in 44 L water) was added over a minimum of 15 min while maintaining the temperature between 20 and 25° C. and stirred for 20 min. The phases were separated and washed as before with a solution of sodium bisulfate (5.6 kg of NaHSO4 in 44 L water). The resulting organic phase was washed with a sodium bicarbonate solution (4.0 kg in 44 L water) and water (2×47 L). The organic phase was concentrated using a maximum jacket temperature of 40° C. until 62 kg remained in the reactor. Heptane (186 L) is added over a minimum of 20 min while maintaining the temperature between 35 and 40° C. The mixture was concentrated using a maximum jacket temperature of 40° C. until 70 kg remained in the reactor. The mixture was cooled to 0 to 5° C. over a minimum of 3 h and stirred for 1 h at 0 to 5° C. The mixture was filtered and washed with heptane at 0 to 5° C. (2×15 L). The wet cake was dried under vacuum at 25 to 30° C. to provide 20.9 kg (74% yield of 7. $^1$H NMR (300 MHz, CDCl$_3$) δ 4.70 (s, 1H), 3.92 (d, J=Hz, 2H), 2.22 (m, 1H), 1.45 (s, 9H); Elemental Anal. Calcd. for C$_8$H$_{13}$NO$_2$: C, 61.91; H, 8.44; N, 9.03; O, 20.62. Found: C, 61.99; H, 8.36; N, 9.11; O, 20.54.

Step 2: tert-butyl {3-[4-chloro-2-(2-fluoro-6-methoxybenzoyl)phenyl]prop-2-yn-1-yl}carbamate (8)

Into a reactor was added 3 (15.0 kg, 38.4 mol), 7 (7.2 kg, 46.4 mol) and cyclohexane (230 L). The suspension was degassed three times for at least 3 min each time using a vacuum-nitrogen cycle. Diethylamine (8.6 kg, 119 mol) was added and the reaction mixture was heated to 28 to 33° C. Dichlorobis(triphenylphosphine)palladium (II) (0.134 kg, 0.192 mol) and copper (II) iodide (0.037 kg, 0.192 mol) were added and the mixture was stirred at 28 to 33° C. for at least 15 h until ≥99.0% conversion was obtained by HPLC analysis. Water (68 L) followed by MTBE (92 L) were added. The reaction mixture was heated to 45 to 50° C. and stirred for a minimum of 30 min and until all solids fully dissolved. The phases were separated at 45 to 50° C. and the organic phase was washed with water (2×68 L) at 45 to 50° C. The resulting organic phase was filtered and the reactor was rinsed with MTBE (32 L) at 45 to 50° C. The rinse was then transferred to the second reactor containing the filtrate via the filter membrane. The combined filtrate was concentrated under vacuum using a jacket temperature of 45 to 50° C. until 225 kg remained in the reactor. The mixture was cooled to 35 to 40° C. and a slurry of seed crystals (10 g of 8 in 500 mL cyclohexane) was added. The reaction mixture was stirred for 60 min at 35 to 40° C. and concentrated under vacuum using a jacket temperature of 45 to 50° C. until 144 kg remained in the reactor. The mixture was cooled to 18 to 23° C. over a minimum of 2 h and stirred for an additional 2 h at 18 to 23° C. The resulting suspension was filtered and washed with cyclohexane (2×53 L). The wet cake was dried under vacuum at 40 to 45° C. to provide 16.0 kg (80% yield) of 8. $^1$H NMR (300 MHz, CDCl$_3$) δ 7.72 (s, 1H), 7.41 (m, 3H), 6.77 (m, 2H), 4.43 (s, 1H), 3.88 (d, J=5.3 Hz, 2H), 3.74 (s, 3H), 1.46 (s, 9H); MS (ESI) m/z 318.4 (M+H$^+$-Boc, 23%), 362.4 (M+H$^+$-t-butyl cation, 20%).

Step 3: 8-chloro-4-[(dimethylamino)methylene]-1-(2-fluoro-6-methoxyphenyl)-3,4-dihydro-5H-2-benzazepin-5-one (9)

Trifluoroacetic acid (158 L) and water (8.3 L) were added to a reactor. A solution of 8 (37.8 kg, 90.5 mol) in dichloromethane (63 L) was added via a second reactor to the trifluoroacetic acid solution over a minimum of 60 min while maintaining the temperature between 20 and 30° C. The reactor containing the solution of 8 was rinsed with dichloromethane (19 L) and transferred to the reaction mixture while maintaining the temperature between 20 and 30° C. The mixture was heated to 30 to 35° C. and stirred for at least 19 h until ≥98.0% conversion was obtained by HPLC analysis. The mixture was concentrated under vacuum at 35 to 45° C. until 76 to 79 kg remained in the reactor. Dichloromethane (424 L) was added while maintaining the internal temperature between 20 and 30° C. N,N-Diisopropylethylamine (64 kg, 495 mol) was added over a minimum of 30 min while maintaining the temperature between 20 and 30° C. If the pH was <8.0 then 5 L portions of N,N-diisopropylethylamine were added until the pH was ≥8.0. The mixture was stirred at 20 to 30° C. for a minimum of 2 h until ≥99.0% conversion was obtained by HPLC analysis. Water (378 L) was added while maintaining the temperature between 20 and 25° C. and stirred for 30 min. The phases were separated and the organic phase was washed with a 10% w/w brine solution (38 kg NaCl in 340 kg of water). The phases were separated and the organic phase was dried with sodium sulfate (5.4 kg) for a minimum of 30 min at 20 to 25° C. The mixture was filtered and the reactor that contained the sodium sulfate mixture was rinsed with additional dichloromethane (27 L) and filtered. Dimethylformamide dimethylacetal (152 kg, 1276 mol) was added to the combined filtrate over a minimum of 30 min while maintaining the temperature between 20 and 30° C. The mixture was warmed to 37 to 42° C. and stirred for a minimum of 20 h until ≥99.0% conversion was obtained by HPLC analysis. The reaction mixture was concentrated under vacuum using a jacket temperature of 40 to 45° C. until 234 to 252 kg remained in the reactor. MTBE (355 L) was added at 35 to 40° C. and the resulting mixture was concentrated under vacuum using a jacket temperature of 40 to 45° C. until 414 to 432 kg remained in the reactor. The suspension was cooled to 20 to 25° C. over a minimum of 3 h and stirred for an additional 2 h. The suspension was filtered and washed at 20 to 25° C. while stirring with MTBE (2×50 L) followed by acetone (2×101 L). The wet cake was dried under vacuum at 35 to 45° C. to provide 28.0 kg (83% yield) of 9. $^1$H NMR (300 MHz, DMSO-$d_6$) δ 7.87 (d, J=8.2 Hz, 1H), 7.63 (s, 1H), 7.58 (d, J=9.4 Hz, 1H), 7.42 (dd, J=6.96, 8.2 Hz, 1H), 6.94 (m, 2H), 4.83 (d, J=12.9 Hz, 1H), 3.44 (d, J=12.9 Hz, 2H), 3.31 (s, 3H), 3.22 (s, 6H); MS (ESI) m/z 373.2 (M+H$^+$, 100%).

Step 4: 4-{[9-chloro-7-(2-fluoro-6-methoxyphenyl)-5H-pyrimido[5,4-d][2]benzazepin-2-yl]amino}-2-methoxybenzoic acid (Formula II)

Into a reactor was added 6 (3.81 kg, 15.5 mol), potassium carbonate (4.3 kg, 31.1 mol), 9 (5.27 kg, 14.1 mol) and methanol (63 L). The suspension was warmed to 50 to 55° C. and stirred for a minimum of 24 h until ≥96.0% conversion was obtained by HPLC analysis. Methanol (10 L) and water (37 L) were added while maintaining the temperature between 50 and 55° C. The pH of the mixture was adjusted to 3.0 to 4.0 using 7% w/w HCl (prepared from 7.0 kg of concentrated HCl and 24 L of water) while maintaining the temperature between 50 and 55° C. The suspension was cooled to 20 to 25° C. over a minimum of 1 h and stirred for at least 60 min. The resulting suspension was filtered and washed with water (2×26.3 L) at 50 to 55° C. and methanol (2×10 L) at 20 to 25° C. The wet cake was dried at 45 to 50° C. under vacuum to provide 5.85 kg (80% yield) of Formula (II). $^1$H NMR (300 MHz, DMSO-$d_6$) δ 12.07 (s, 1H), 10.22 (s, 1H), 8.72 (s, 1H), 8.29 (d, J=8.8 Hz, 1H), 7.95 (s, 1H), 7.80 (dd, J=2.4, 8.9 Hz, 1H), 7.70 (d, J=8.8 Hz, 1H), 7.39 (m, 3H), 7.21 (s, 1H), 6.89 (s, 2H), 3.82 (s, 6H); MS (ESI) m/z MS (ESI) m/z 517.2 (M−H$^+$, 45%).

Step 5:
Method A: sodium 4-{[9-chloro-7-(2-fluoro-6-methoxyphenyl)-5H-pyrimido[5,4-d][2]benzazepin-2-yl]amino}-2-methoxybenzoate polymorph Form 2

Compound Formula (II) (130 g, 0.244 mol), absolute ethanol (975 mL, 7.5 volumes) and water (715 mL, 5.5 volumes) were added to a reactor and warmed to between 69 and 74° C. A 1.0 M sodium hydroxide solution in water (260 ML, 2.0 volumes, 0.260 mol) was added dropwise while maintaining the temperature between 69 and 74° C. The pH of the reaction mixture was continuously monitored and the addition was stopped once the pH reached 9.5 to 10.5 (preferably 9.8 to 10). The mixture was stirred for at least 1h at 69 to 74° C. and if the pH decreased from the defined range then additional portions of the above 1.0 M NaOH solution were added until a pH of 9.5 to 10.5 was obtained. The reaction mixture was warmed to an internal temperature of 72 to 77° C. The solution was filtered and transferred to a separate reactor while maintaining an internal temperature of 69 to 77° C. Absolute ethanol (1690 mL, 13 volumes) preheated to 69 to 74° C. was filtered and added to the reaction mixture while maintaining a reaction mixture temperature of 69 to 74° C. Compound Formula (I) (1.30 g) was added and stirred for at least 15 min at 62 to 67° C. and the reaction mixture was then heated to 69 to 74° C. Seed crystals were present. The resulting suspension was concentrated at 60 to 74° C. under vacuum until 910 mL (7 volumes) of solvent were removed. Absolute ethanol (910 mL, 7 volumes) preheated to 69 to 74° C. was filtered and added to the reaction mixture while maintaining a reaction mixture temperature of 69 to 74° C. The resulting suspension was concentrated at 60 to 74° C. under vacuum until 910 mL (7 volumes) of solvent were removed. The addition of 7 volumes of absolute ethanol followed by concentration as described above was repeated at least four times. An In Process Control was obtained for % w/w of water by KF analysis. The addition of 7 volumes of absolute ethanol followed by concentration was repeated until a KF of ≤15.0% w/w was reached. The reaction mixture was cooled to 20 to 25° C. over a minimum of 2.5 to 3 h and stirred for at least 1 h at 20 to 25° C. and the suspension was filtered. The solid was washed twice with stirring using absolute ethanol (2×486.5 mL, 3.74 volumes). The wet cake was dried under vacuum at 40 to 45° C. until the residual ethanol content was ≤0.4% w/w as determined by GC analysis. A total of 96.8 g (71% yield) of compound Formula (I) was obtained. $^1$H NMR (300 MHz, DMSO-$d_6$) δ 9.72 (s, 1H), 8.61 (s, 1H), 8.25 (d, J=7.6, 1H), 7.79 (dd, J=2.3, 8.8 Hz, 1H), 7.58 (s, 1H), 7.40 (dd, J=8.2, 15.2 Hz, 1H), 7.25 (d, J=8.2, 1H), 7.17 (m, 2H), 6.88 (s, 2H), 3.69 (s, 3H), 3.31 (s, 3H); MS (ESI) m/z 517.2 (M−H$^+$, 45%).

Method B: sodium 4-{[9-chloro-7-(2-fluoro-6-methoxyphenyl)-5H-pyrimido[5,4-d][2]benzazepin-2-yl]amino}-2-methoxybenzoate polymorph Form 1

To a stirred suspension of Compound Formula (II) (98.0 g, 190 mmol) in ethanol (2.0 L) was added 1.044 M Sodium hydroxide in water (199 mL). The resultant homogeneous solution was stirred for 1 hour, during which time a thick precipitate formed. The product was collected by filtration, and washed with ethanol (0.5 L) and diethyl ether (1.0 L). The resultant solid was dried in vacuo at 60-70° C. for 4 days to provide 88.6 g (86.8%) of compound Formula (I) as a light tan solid, mp 225° C. (decomp). $^1$H NMR (DMSO-$d_6$) δ 9.86 (s, 1H), 8.60 (s, 1H), 8.29 (d, 1H), 7.79 (dd, 1H), 7.60 (br s, 1H), 7.40 (dd, 1H), 7.29 (d, 1H), 7.25-7.15 (m, 2H), 6.9 (br s, 2H), 4.9 (br s, 1H), 3.8 (br s, 1H), 3.70 (s, 3H), 3.35 (br s, 3H); MS m/z 519 (M$^+$–Na+H, 100%); CHN Anal. Calcd. for $C_{27}H_{19}ClFN_4NaO_4$0.33 EtOH1.3H$_2$O: C, 57.33; H, 4.10; N, 9.67. Found C, 57.14; H, 3.99; N, 9.65.

Method C: amorphous sodium 4-{[9-chloro-7-(2-fluoro-6-methoxyphenyl)-5H-pyrimido[5,4-d][2]benzazepin-2-yl]amino}-2-methoxybenzoate 1.0 g of sodium 4-{[9-chloro-7-(2-fluoro-6-methoxyphenyl)-5H-pyrimido[5,4-d][2]benzazepin-2-yl]amino}-2-methoxybenzoate Form 2 was dissolved in 350 mL of water at 65° C. The solution was frozen in a solid CO$_2$/acetone slurry and then freeze-dried. An amorphous hygroscopic, fluffy solid was obtained.

Example 4

Synthesis of sodium 4-{[9-chloro-7-(2-fluoro-6-methoxyphenyl)-5H-pyrimido[5,4-d][2]benzazepin-2-yl]amino}-2-methoxybenzoate polymorph Form 4.

2.5 mL of ethanol was added to 50 mg of amorphous freeze-dried sodium 4-{[9-chloro-7-(2-fluoro-6-methoxyphenyl)-5H-pyrimido[5,4-d][2]benzazepin-2-yl]amino}-2-methoxybenzoate (pre-dried for 1 hour under vacuum at 50° C.) in a screw-top vial. The vial was shaken for 1 week with alternating 4 hour periods at 50° C. and ambient temperature. Form 4 was isolated by filtration. XRPD data for Form 4 is shown in FIG. 7 and Table 3.

Example 5

Synthesis of sodium 4-{[9-chloro-7-(2-fluoro-6-methoxyphenyl)-5H-pyrimido[5,4-d][2]benzazepin-2-yl]amino}-2-methoxybenzoate polymorph Form 6.

3.0 mL of methanol was added to 100 mg of sodium 4-{[9-chloro-7-(2-fluoro-6-methoxyphenyl)-5H-pyrimido[5,4-d][2]benzazepin-2-yl]amino}-2-methoxybenzoate Form 2 in a screw-top vial. The vial was shaken for 72 hours with alternating 4 hour periods at 50° C. and ambient temperature. Form 6 was isolated by filtration. XRPD data for Form 6 is shown in FIG. 8 and Table 4; DSC data is shown in FIG. 9; TGA data is shown in FIG. 10; GVS data is shown in FIG. 11.

Example 6

Synthesis of sodium 4-{[9-chloro-7-(2-fluoro-6-methoxyphenyl)-5H-pyrimido[5,4-d][2]benzazepin-2-yl]amino}-2-methoxybenzoate polymorph Form 11.

3.0 mL of methanol was added to 100 mg of sodium 4-{[9-chloro-7-(2-fluoro-6-methoxyphenyl)-5H-pyrimido[5,4-d][2]benzazepin-2-yl]amino}-2-methoxybenzoate Form 2 in a screw-top vial. The vial was shaken for 72 hours with alternating 4 hour periods at 50° C. and ambient temperature. The resulting slurry was filtered and the filtrate retained. 10 mL of the anti-solvent cyclohexane was added, but no precipitation occurred. The solution was allowed to evaporate to afford a mixture of Form 11 and Form 24. XRPD data for Form 11 is shown in FIG. 12 and Table 5; DSC data is shown in FIG. 13.

Example 7

Synthesis of sodium 4-{[9-chloro-7-(2-fluoro-6-methoxyphenyl)-5H-pyrimido[5,4-d][2]benzazepin-2-yl]amino}-2-methoxybenzoate polymorph Form 12.

10 mL of 90% ethanol/10% water solution was added to 100 mg of sodium 4-{[9-chloro-7-(2-fluoro-6-methoxyphenyl)-5H-pyrimido[5,4-d][2]benzazepin-2-yl]amino}-2-methoxybenzoate Form 2 in a screw-top vial. The vial was heated to 50° C. and shaken for 2 hours. The resulting slurry was filtered at 50° C. and the filtrate retained. The filtrate was stored at 4° C. for 17 hours, but no precipitation occurred. The vial was uncapped to allow evaporation to afford Form 12. XRPD data for Form 12 is shown in FIG. 14 and Table 6; DSC data is shown in FIG. 15; TGA data is shown in FIG. 16.

Example 8

Synthesis of sodium 4-{[9-chloro-7-(2-fluoro-6-methoxyphenyl)-5H-pyrimido[5,4-d][2]benzazepin-2-yl]amino}-2-methoxybenzoate polymorph Form 24.

200 mg of 4-{[9-chloro-7-(2-fluoro-6-methoxyphenyl)-5H-pyrimido[5,4-d][2]benzazepin-2-yl]amino}-2-methoxybenzoic acid was stirred in 4 mL of ethanol in a screw-top vial. 1.1 mol equivalents of sodium hydroxide solution (406 µL, 1.044 M in water) were added. The solid dissolved followed by formation of a yellow precipitate. The sample was a mixture of Form 4 and Form 24. The solid was washed with 10 mL of ethanol and 20 mL of diethyl ether, and dried under vacuum at 70° C. for 2 days, and at 60° C. for a further 3 days to give Form 24. XRPD data for Form 24 is shown in FIG. 17 and Table 7; DSC data is shown in FIG. 18; TGA data is shown in FIG. 19.

While the foregoing invention has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the invention, which is to be defined by the appended claims rather than by the specific embodiments.

The patent and scientific literature referred to herein establishes knowledge that is available to those with skill in the art. Unless otherwise defined, all technical and scientific terms used herein have the same meaning as commonly understood by one of ordinary skill in the art to which this invention belongs. The issued patents, applications, and references that are cited herein are hereby incorporated by reference to the same extent as if each was specifically and individually indicated to be incorporated by reference. In the case of inconsistencies, the present disclosure, including definitions, will control.

What is claimed is:

1. A crystalline form of the compound of formula (I):

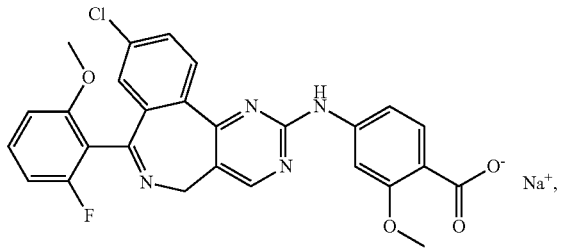

(I)

wherein the crystalline form is Form 4, characterized by an X-ray powder diffraction pattern having peaks at 2θ angles of 13.27°, 22.96° and 25.89°.

2. The crystalline form of claim 1, characterized by an X-ray powder diffraction pattern substantially similar to FIG. 7.

3. A crystalline form of the compound of formula (I):

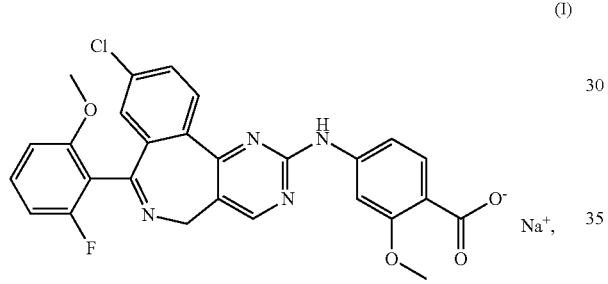

(I)

wherein the crystalline form is Form 6, characterized by at least one of the following features:
- an X-ray powder diffraction pattern having peaks at 2θ angles of 16.01°, 17.47°, 21.23° and 23.43°;
- a differential scanning calorimetry (DSC) profile substantially similar to FIG. 9;
- a thermal gravimetric analysis (TGA) profile substantially similar to FIG. 10; and
- a gravimetric vapor sorption (GVS) profile substantially similar to FIG. 11.

4. The crystalline form of claim 3, characterized by at an X-ray powder diffraction pattern having peaks at 2θ angles of 11.62°, 16.01°, 17.47°, 21.23°, 23.43°, and 29.38°.

5. The crystalline form of claim 3, characterized by an X-ray powder diffraction pattern substantially similar to FIG. 8.

6. The crystalline form of claim 3, characterized by at least two of the following features:
- an X-ray powder diffraction pattern having peaks at 2θ angles of 16.01°, 17.47°, 21.23° and 23.43°;
- a differential scanning calorimetry (DSC) profile substantially similar to FIG. 9;
- a thermal gravimetric analysis (TGA) profile substantially similar to FIG. 10; and
- a gravimetric vapor sorption (GVS) profile substantially similar to FIG. 11.

7. A crystalline form of the compound of formula (I):

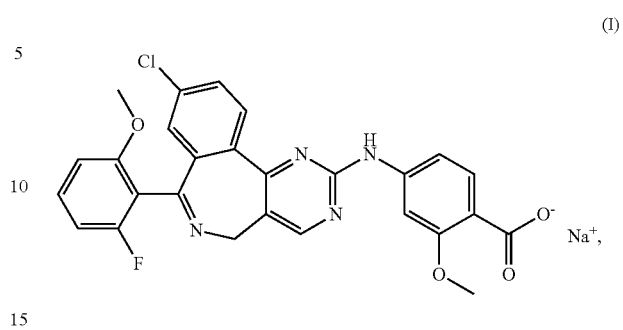

(I)

wherein the crystalline form is Form 11, characterized by at least one of the following features:
- an X-ray powder diffraction pattern having peaks at 2θ angles of 13.03°, 26.21° and 27.08°; and
- a differential scanning calorimetry (DSC) profile substantially similar to FIG. 13.

8. The crystalline form of claim 7, characterized by an X-ray powder diffraction pattern having peaks at 2θ angles of 13.03°, 15.72°, 25.66°, 26.21°, and 27.08°.

9. The crystalline form of claim 7, characterized by at least one an X-ray powder diffraction pattern substantially similar to FIG. 12.

10. The crystalline form of claim 7, characterized by both of the following features:
- an X-ray powder diffraction pattern having peaks at 2θ angles of 13.03°, 26.21° and 27.08°; and
- a differential scanning calorimetry (DSC) profile substantially similar to FIG. 13.

11. A crystalline form of the compound of formula (I):

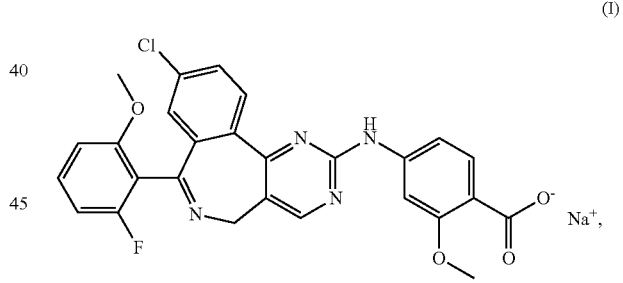

(I)

wherein the crystalline form is Form 12, characterized by at least one of the following features:
- an X-ray powder diffraction pattern having peaks at 2θ angles of 12.72°, 21.26°, 21.89°, and 25.57°;
- a differential scanning calorimetry (DSC) profile substantially similar to FIG. 15; and
- a thermal gravimetric analysis (TGA) profile substantially similar to FIG. 16.

12. The crystalline form of claim 11, characterized by an X-ray powder diffraction pattern having peaks at 2θ angles of 12.72°, 13.46°, 21.26°, 21.89°, 25.57°, and 29.50°.

13. The crystalline form of claim 11, characterized by an X-ray powder diffraction pattern substantially similar to FIG. 14.

14. The crystalline form of claim 11, characterized by at least two of the following features:
- an X-ray powder diffraction pattern having peaks at 2θ angles of 12.72°, 21.26°, 21.89°, and 25.57°;

a differential scanning calorimetry (DSC) profile substantially similar to FIG. 15; and
a thermal gravimetric analysis (TGA) profile substantially similar to FIG. 16.

15. A crystalline form of the compound of formula (I):

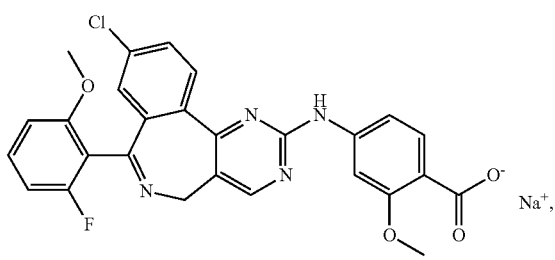

(I)

wherein the crystalline form is Form 24, characterized by at least one of the following features:
an X-ray powder diffraction pattern having peaks at 2θ angles of 10.93°, 15.67°, 22.90°, 23.84°, and 26.91°;
a differential scanning calorimetry (DSC) profile substantially similar to FIG. 18; and
a thermal gravimetric analysis (TGA) profile substantially similar to FIG. 19.

16. The crystalline form of claim 15, characterized by an X-ray powder diffraction pattern having peaks at 2θ angles of 10.93°, 15.67°,19.76°, 22.05°, 22.90°, 23.38°, 23.84°, and 26.91°.

17. The crystalline form of claim 15, characterized by an X-ray powder diffraction pattern substantially similar to FIG. 17.

18. The crystalline form of claim 15, characterized by at least two of the following features:
an X-ray powder diffraction pattern having peaks at 2θ angles of 10.93°, 15.67°, 22.90°, 23.84°, and 26.91°;
a differential scanning calorimetry (DSC) profile substantially similar to FIG. 18; and
a thermal gravimetric analysis (TGA) profile substantially similar to FIG. 19.

19. A solid pharmaceutical composition comprising at least one of the crystalline forms according to any one of claim 1, 3, 7, 11, or 15, and at least one pharmaceutically acceptable carrier or diluent.

20. A method for treating cancer comprising the administration of a therapeutically effective amount of at least one of the crystalline forms according to any one of claim 1, 3, 7, 11, or 15, to a patient in need thereof, wherein the cancer is selected from the group consisting of ovarian cancer, T-cell lymphoma and lung cancer.

* * * * *